US011219738B2

(12) United States Patent
Islava et al.

(10) Patent No.: US 11,219,738 B2
(45) Date of Patent: *Jan. 11, 2022

(54) ADJUSTABLE RESUSCITATION DEVICE AND METHOD FOR USING THE SAME

(71) Applicants: Steve Islava, Newport Beach, CA (US); John Guy Cazort, III, Corona del Mar, CA (US); Richard A. Van Auken, Aliso Viejo, CA (US)

(72) Inventors: Steve Islava, Newport Beach, CA (US); John Guy Cazort, III, Corona del Mar, CA (US); Richard A. Van Auken, Aliso Viejo, CA (US)

(73) Assignee: Care 2 Innovations Inc., Irvine, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 16/256,351

(22) Filed: Jan. 24, 2019

(65) Prior Publication Data
US 2020/0078550 A1 Mar. 12, 2020

Related U.S. Application Data

(63) Continuation-in-part of application No. 16/127,596, filed on Sep. 11, 2018.

(51) Int. Cl.
*A61M 16/20* (2006.01)
*A61M 16/00* (2006.01)

(52) U.S. Cl.
CPC ...... *A61M 16/201* (2014.02); *A61M 16/0075* (2013.01); *A61M 16/0084* (2014.02);
(Continued)

(58) Field of Classification Search
CPC .......... A61M 16/0081; A61M 16/0075; A61M 16/0084; A61M 16/0078
See application file for complete search history.

(56) References Cited

U.S. PATENT DOCUMENTS 5,345,929 A * 9/1994 Jansson ............. A61M 16/0075
128/205.13
5,628,305 A * 5/1997 Melker ............. A61M 16/0048
128/202.29

(Continued)

FOREIGN PATENT DOCUMENTS

EP 0421007 A1 * 4/1991 ........ A61M 16/0084

*Primary Examiner* — Margaret M Luarca
(74) *Attorney, Agent, or Firm* — Marcus C. Dawes

(57) ABSTRACT

A device and method for adjusting a tidal breath delivered to a patient. The device includes a moving frame which is configured to move over a stationary frame that is nested within the moving frame itself. Disposed between the moving frame and the stationary frame is a compressible bellows which delivers a tidal breath to the patient each time the moving frame is passed over the stationary frame. The specific volume of the tidal breath that is delivered may adjusted according to the estimated weight of the patient, thereby preventing over inflation of the patient's lungs while undergoing treatment. To adjust the tidal breath volume, the user quickly changes the relative position of a slide selector which dictates the range of possible movement for the bellows to be compressed, thereby limiting the volume of air/oxygen which may be delivered by the bellows.

18 Claims, 22 Drawing Sheets

(52) U.S. Cl.
CPC ... *A61M 16/208* (2013.01); *A61M 2202/0208* (2013.01); *A61M 2205/3379* (2013.01)

(56) References Cited

U.S. PATENT DOCUMENTS

| | | |
|---|---|---|
| 8,443,804 B2 | 5/2013 | Lee |
| 9,861,775 B1* | 1/2018 | Farmer ............. A61M 16/0084 |
| 2008/0015475 A1* | 1/2008 | Lau ..................... A61M 16/125 |
| | | 601/41 |
| 2009/0145437 A1* | 6/2009 | Halpern ............ A61M 16/0616 |
| | | 128/206.21 |

* cited by examiner

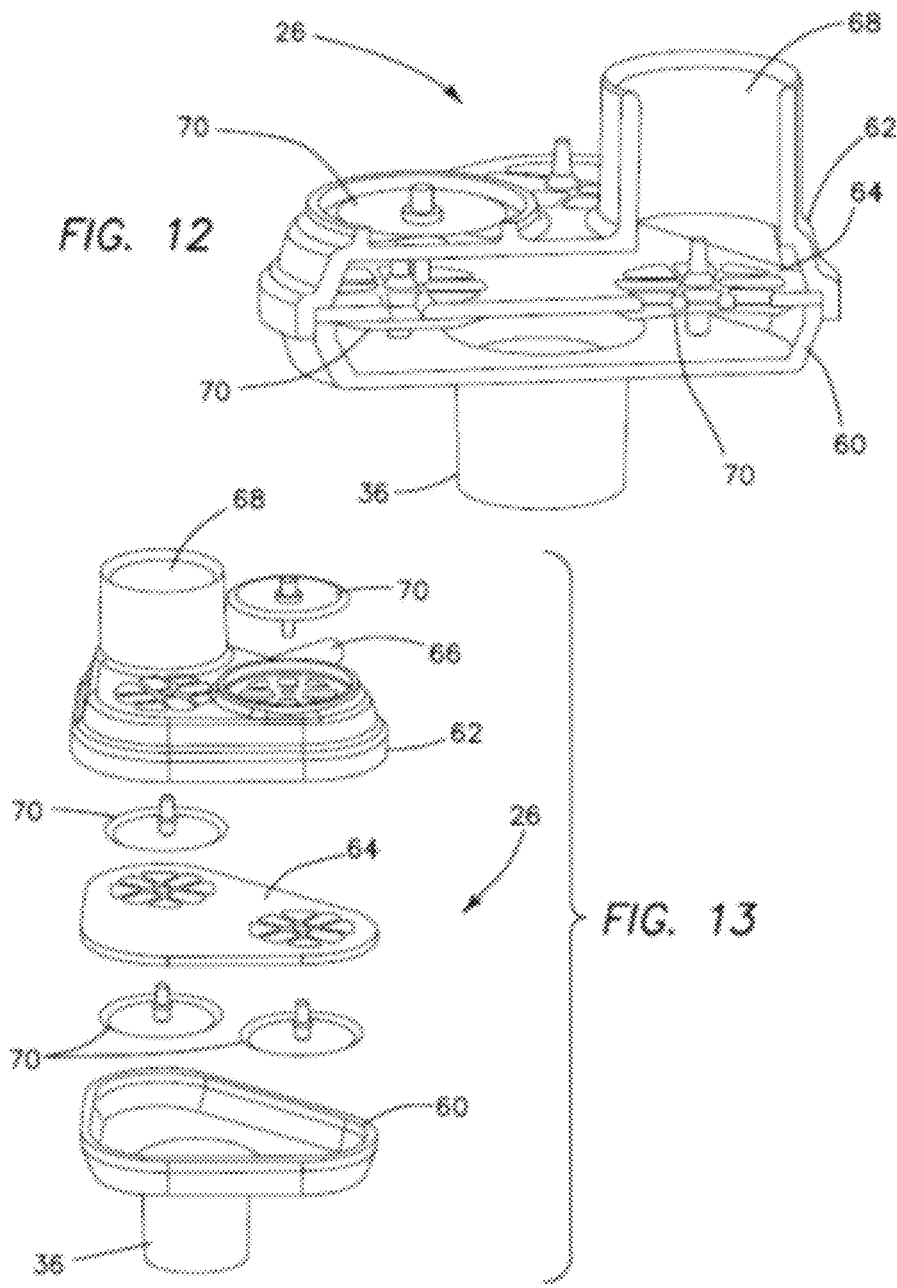

ADJUSTABLE RESUSCITATION DEVICE AND METHOD FOR USING THE SAME

BACKGROUND

Field of the Technology

The invention relates to the field of emergency medical devices, particularly to mobile resuscitation devices.

Description of the Prior Art

Resuscitation devices have long been used by emergency response personnel and other medical professionals to forcibly send air or oxygen into the lungs of an injured or unconscious patient. Many of these devices take the form of a resuscitation bag that is coupled to a face mask which is placed over the patient's nose and mouth, attached to an endotracheal tube, or other airway device. The bag also typically comprises a one-way directional valve which is in turn coupled to a reservoir, an oxygen source, or is instead open to the ambient environment. After the face mask has been properly placed, the EMT or medical professional squeezes or compresses the bag which forces air contained within the bag to travel through the face mask and enter the patient's oral airway. When the medical professional releases the bag or otherwise relaxes their grip, air from the environment or the reservoir enters the bag through the one-way directional to fill the vacuum created within the bag. The medical professional continues to ventilate the patient by repeatedly squeezing the bag and delivering air to the patient's lungs for as long as their specific treatment requires.

However, as has become increasingly accepted within the medical community, providing tidal volumes to a patient which are too large or at too high a pressure can be harmful to the patient and can in fact produce lung injury. For example, over inflating a child or adult causes air to enter the stomach or may rupture the alveoli. Additionally, it is very easy to over inflate a patient in an emergency situation when the added stress and surrounding circumstances of the emergency can cause unintentional exuberance on the part of the treating medical professional. Previously, it was thought that 10 to 15 ml of air/oxygen per kilogram of the patient weight was thought to be sufficient, however recently it has become apparent that tidal volumes of only 6 to 8 ml of air/oxygen per kilogram of the patient weight are ideal for avoiding further acute lung injury in the patient.

It is therefore critical for a patient requiring ventilation that the resuscitation device provides a tidal volume which matches the patient's specific lung size. In other words, the resuscitation device must consistently and reliably deliver a volume of air/oxygen which is large enough to provide the patient sufficient ventilation but not so large that the patient's lungs are injured. This can be difficult however using a resuscitation bag since the volume of air which is delivered to the patient is dictated by the amount or how hard the medical professional squeezes the bag. The medical professional using a resuscitation bag must therefore estimate the proper amount of air/oxygen by observing the rise and fall of the chest as well as resistance caused by the lungs filling. After estimating a proper amount, the EMT must then actually compress the bag to the required degree in order to deliver that desired tidal volume each and every time, a process which the medical professional has no ability to verify since many resuscitation devices do not have a means for measuring or displaying the volume of air which is squeezed from the bag. Because the specific volume of air can vary significantly each time the medical professional compresses the bag, it is almost impossible for the medical professional to deliver a consistent tidal volume to the patient which is correctly keyed to their specific lung capacity.

Several resuscitation devices exist which comprise several different sized bags, wherein each bag is configured to deliver a different tidal volume when compressed. For example, the resuscitation device comprises a face mask which may detached and reattached to an appropriately sized removable bag, namely a large bag for adults and a smaller bag for smaller adults or children. This type of device can be problematic however for EMTs and other medical professionals who work in confined areas such as ambulances and field hospitals where storage space is at a premium, thus making the storage of multiple resuscitation bags inconvenient if not impractical. Furthermore, EMTs and other trained medical professionals, who are often operating under emergency conditions need a fast, reliable way to deliver the correct tidal volume with a minimum of extraneous effort so that the patient can be treated properly as soon as possible.

BRIEF SUMMARY

The current invention is a resuscitation device which limits a tidal volume which is delivered to a patient. The device principally includes a stationary frame, a moving frame which at least partially encloses the stationary frame, and a bellows comprising two opposing ends, a first opposing end coupled to the stationary frame and a second opposing end coupled to the moving frame. Additionally, a slide selector is disposed between the moving frame and the stationary frame. An oxygen valve is coupled to the second opposing end of the bellows while a patient valve is coupled to the stationary frame.

In one embodiment, the slide selector is selectively coupled to a plurality of teeth that are disposed on the moving frame.

In another embodiment, the moving frame includes a slit defined in its top surface, while the slide selector in turn includes a thumb depress and a marker which extend from between the moving frame and the stationary frame through the slit. In this embodiment, the top surface of the moving frame also includes a measurement table disposed on either lateral side of the slit. The top surface of the moving frame also has a measurement table disposed on either lateral side of the slit.

In a related embodiment, the moving frame includes a cavity for accommodating the slide selector and wherein the stationary frame includes a stop which is configured to interact with a flat edge of the slide selector.

In yet another embodiment, the slide selector comprises an upper tine and a lower tine. Specifically, the upper tine and the lower tine are coupled or connected together so as to form a resilient spring. The upper tine of the slide selector also has a pawl and a thumb depress disposed on its proximal end of the upper tine.

In another embodiment, the bellows, which is disposed between the moving frame and the stationary frame, is in fluidic communication with a hollow volume defined within the stationary frame and with the oxygen valve coupled to the second opposing end of the bellows.

In a further embodiment, the stationary frame also includes a handle while the moving frame in turn includes a traverse. The traverse has a concave interior which is specifically configured to accommodate a protrusion that is disposed on the handle.

Additionally, in one particular embodiment the stationary frame includes a stop which is configured to interact with a flat edge disposed on the slide adjuster.

The invention further includes a method for adjusting a tidal volume delivered to a patient by a user with a device. The method includes estimating a weight of the patient, actuating a slide selector located between a moving frame and a stationary frame of the device, and disposing the moving frame at a first position relative to a stationary frame as dictated by the position of the slide selector. Next, the moving frame is moved in a proximal direction toward the patient to a second position relative to the stationary frame so that a volume of oxygen can be delivered to the patient from a bellows which is connected between the moving frame and the stationary frame. The moving frame is then moved in a distal direction away from the patient back to the first position relative to the stationary frame in order to refill the bellows with a new volume of oxygen.

In one embodiment, the method step of actuating the slide selector disposed between a moving frame and a stationary frame of the device specifically includes pushing or pulling the slide selector within a cavity defined within the moving frame.

In another embodiment, actuating the slide selector disposed between a moving frame and a stationary frame of the device specifically includes first pressing downward on a thumb depress disposed on a upper tine of the slide selector in order to move a pawl disposed on the upper tine off of a plurality of teeth disposed on an interior surface of the moving frame. The slide selector is then moved or slid either proximally or distally relative to the moving frame and the stationary frame. The thumb depress is then released to allow the upper tine to move upward and reinsert the pawl into the plurality of teeth disposed on the interior surface of the moving frame. In this embodiment, pushing or pulling the slide selector within the cavity defined within the moving frame also includes simultaneously moving the thumb depress and a marker disposed on the slide selector through a slit that is defined in the moving frame.

In yet another embodiment, the moving frame is moved in a proximal direction toward the patient to a second position relative to the stationary frame by specifically compressing the bellows disposed between the moving frame and the stationary frame.

In a related embodiment, the moving frame is moved in a proximal direction toward the patient relative to the stationary frame specifically includes disposing a concave interior defined within a traverse within the moving frame over a protrusion disposed on a handle within the stationary frame.

In another embodiment, the volume of oxygen is delivered to the patient from the bellows coupled between the moving frame and the stationary frame by directing the volume of oxygen from an oxygen valve integrated into the bellows through a hollow volume defined within the stationary frame and into a patient valve coupled to the stationary frame.

In a further embodiment, the moving frame is moved in the distal direction away from the patient relative to the stationary frame by specifically allowing the bellows to expand which pushes the moving frame distally away from the stationary frame. Also in this embodiment, the bellows are allowed or permitted to expand until a flat edge disposed on the slide selector makes surface contact with a stop that is disposed on the stationary frame.

Finally, in a separate embodiment, the method also includes connecting both a resuscitation bag and an oxygen tube to an oxygen valve that is integrated into a distal end of the bellows.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 12 is a cross-sectional view of the oxygen valve of the resuscitation device.

FIG. 13 is an exploded view of the oxygen valve of the resuscitation device seen in FIG. 12.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
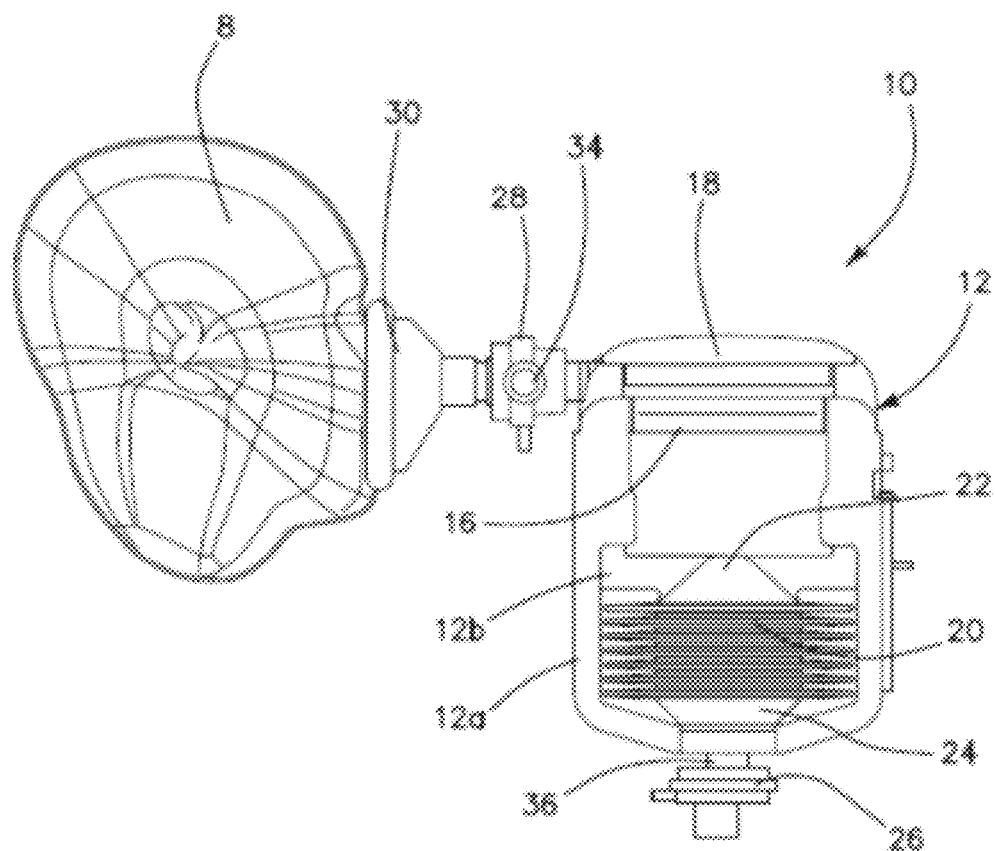
FIG. 1 is a right side perspective view of the current resuscitation device being used on a patient. The resuscitation device is seen during a compression stroke where oxygen is being delivered to the patient.
Figure 2:
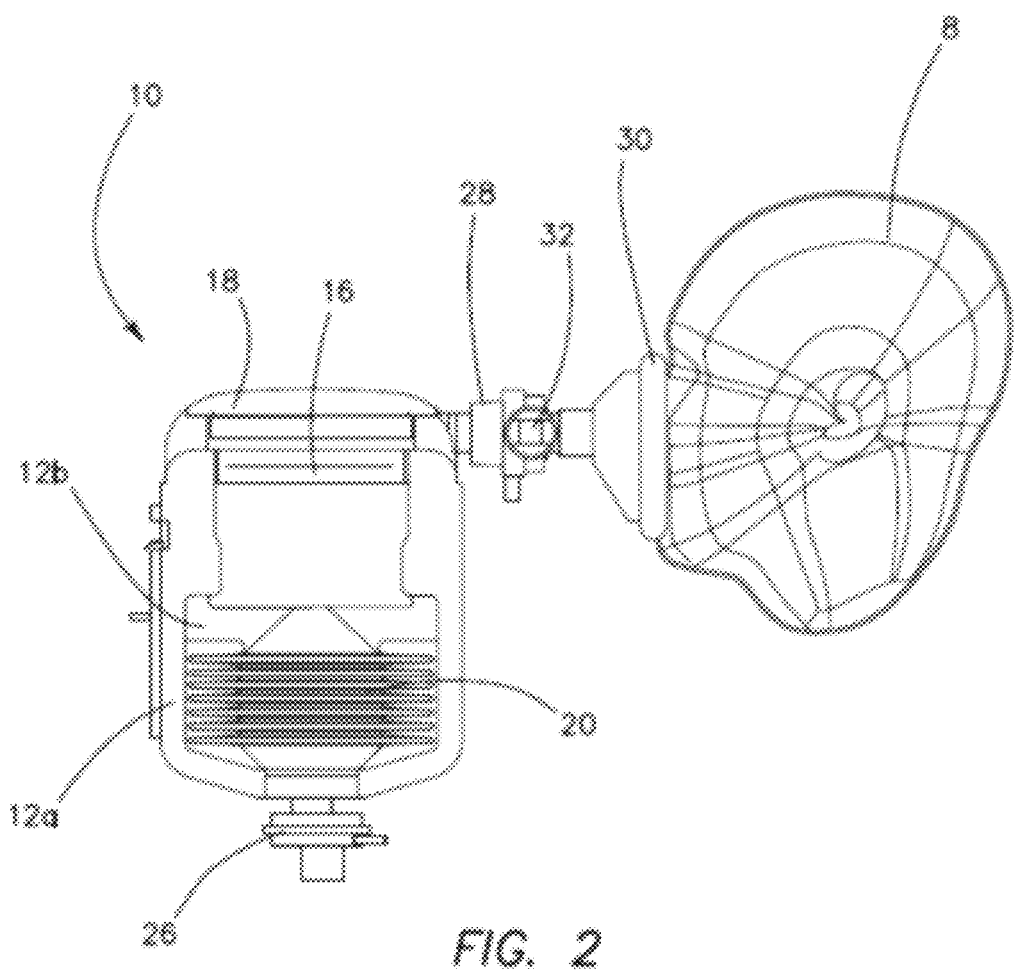
FIG. 2 is a left side perspective view of the resuscitation device seen in FIG. 1.

The current invention is a resuscitation device seen in FIG. 1 and is denoted generally by reference numeral 10. The resuscitation device 10 comprises a substantially U-shaped frame 12 which itself comprises a moving frame 12a and a stationary frame 12b. Disposed across the top of the moving frame 12a is an ergonomic traverse 16 which is contoured to accommodate the hand and fingers of a user, for example an EMT or other medical professional. Disposed across the top portion of the stationary frame 12b in turn is an ergonomic handle 18 that is configured and shaped to be gripped by the palm of the user. The moving frame 12a comprises a hollow interior which accommodates the stationary frame 12b in a nested configuration therein as seen in FIGS. 1-3. The hollow interior of the moving frame 12A allows it to move relative to the stationary frame 12b. Coupled to both the moving frame 12a and the stationary frame 12b is a flexible and extendable bellows 20. Specifically, a top portion 22 of the bellows 20 is incorporated into the stationary frame 12b so that the internal volume of the bellows 20 is in fluidic communication with in an internal hollow volume of the stationary frame 12b. Similarly a bottom portion 24 of the bellows 20 is incorporated into the moving frame 12a so that the internal volume of the bellows 20 is also in fluidic communication with an oxygen valve 26 coupled to the moving frame 12a. The bellows 20 serves as a conduit for oxygen to flow from the oxygen valve 26 to the patient 8 in a series of predetermined tidal breaths as is described in further detail below.

The resuscitation device 10 further comprises a patient valve 28 which may be manipulated or adjusted to regulate the flow of air or oxygen there through as is known in the art. The patient valve 28 is in fluidic communication with the internal volume of the hollow interior of the stationary frame 12B. The patient valve 28 further comprises an exhalation port 32 and a "pop off" valve 34 allowing delivered air or oxygen to escape from the device 10 instead of being forced into the patient's oral airway when a selected pressure threshold has been exceeded. A face mask 30 is in turn removably coupled to the patient valve 28. The face mask 30 is sufficiently sized and shaped to fit comfortably over the nose and mouth of a patient 8 as seen in FIG. 1.

Coupled to the moving frame 12A of the resuscitation device 10 is an oxygen valve 26 which is configured to be coupled to an oxygen tank or other oxygen source, either directly or indirectly through tubing. FIGS. 13 and 12 show an exploded view and a cross sectional view of the oxygen valve 26, respectively. The oxygen valve 26 comprises a bottom half 60 and a top half 62 with a middle portion 64 disposed there between. The bottom half 60 comprises a bellows outlet 36 while the top half 62 comprises an oxygen inlet 66 and a reservoir outlet 68. The oxygen valve 26 is communicated to the internal volume of the bellows 20 via the bellows outlet 36. The oxygen inlet 66 is configured to be coupled to an oxygen source or to tubing which itself is coupled to an oxygen source. The reservoir outlet 68 may accommodate a reservoir such as an oxygen bag or other device (not seen). Disposed in the top half 62 and the middle portion 64 are a plurality of valves 70. Like the patient valve 28, the oxygen valve 26 may be manipulated to regulate the volume and pressure of the oxygen entering the bellows 20 via the valves 70. Like the patient valve 28, the oxygen valve 26 may be manipulated by either the medical professional at the time of use or alternatively, at the point of manufacture to regulate the volume and pressure of the oxygen entering the bellows 20 via the valves 70. The oxygen valve 26 further allows excess oxygen to bleed off or otherwise be expelled from the device 10 if the pressure within the bellows 20, patient valve 28, and/or oxygen valve 26 has exceeded a predetermined threshold value.

Figure 3A:
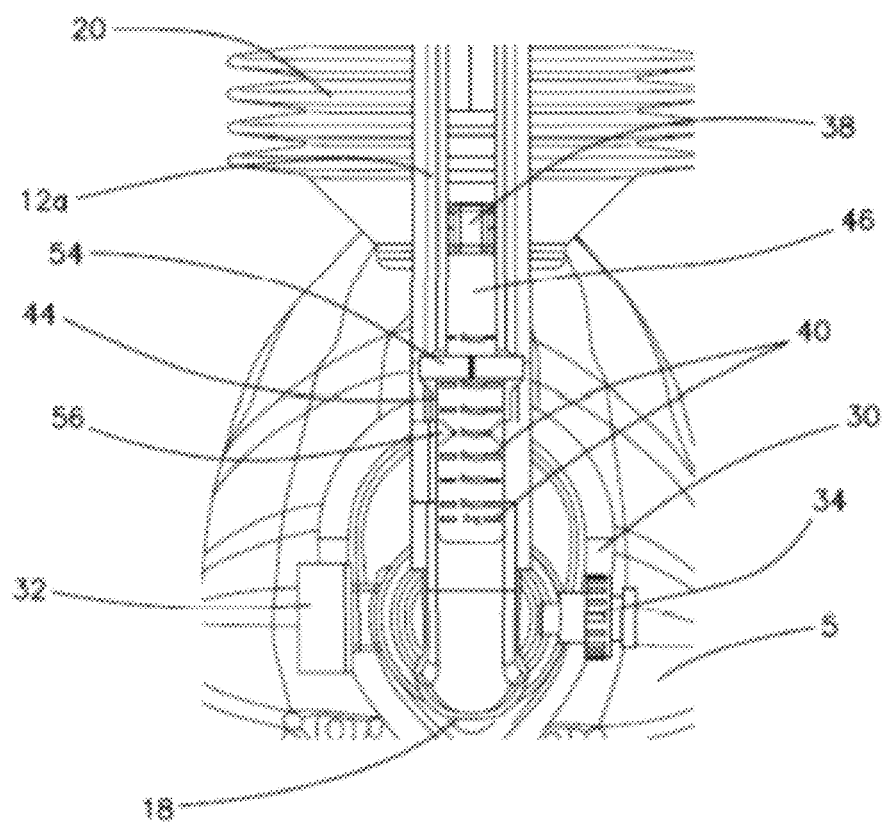
FIG. 3A is a frontal view of the resuscitation device seen in FIG. 1 when the device is set to deliver a tidal volume for a patient weighing 40 kg.
Figure 3B:
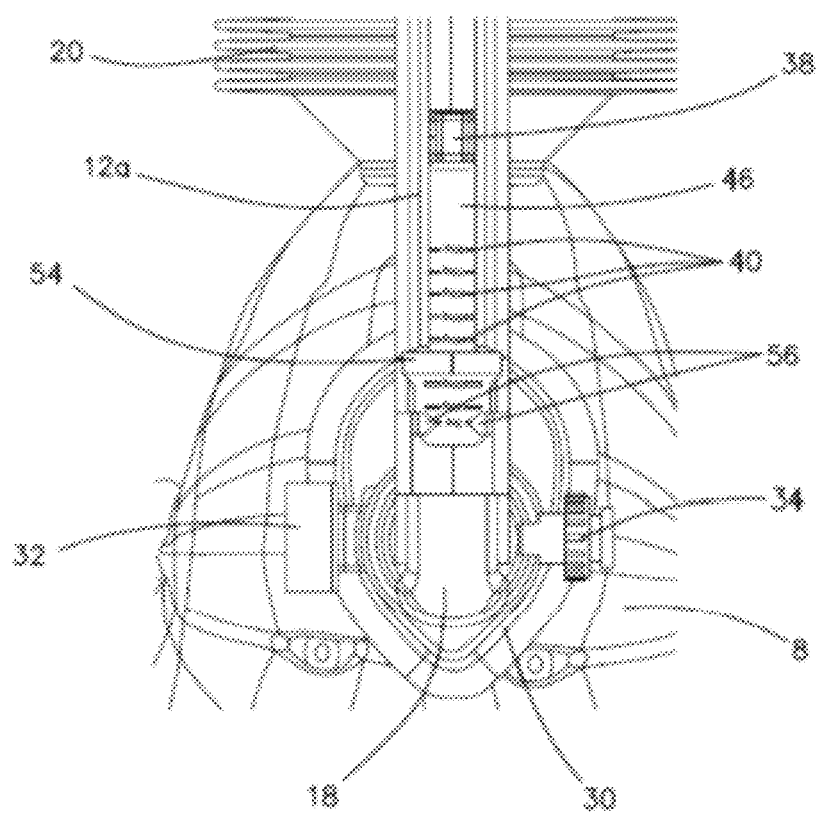
FIG. 3B is a frontal view of the resuscitation device seen in FIG. 1 when the device is set to deliver a tidal volume for a patient weighing 3 kg.
Figure 4:
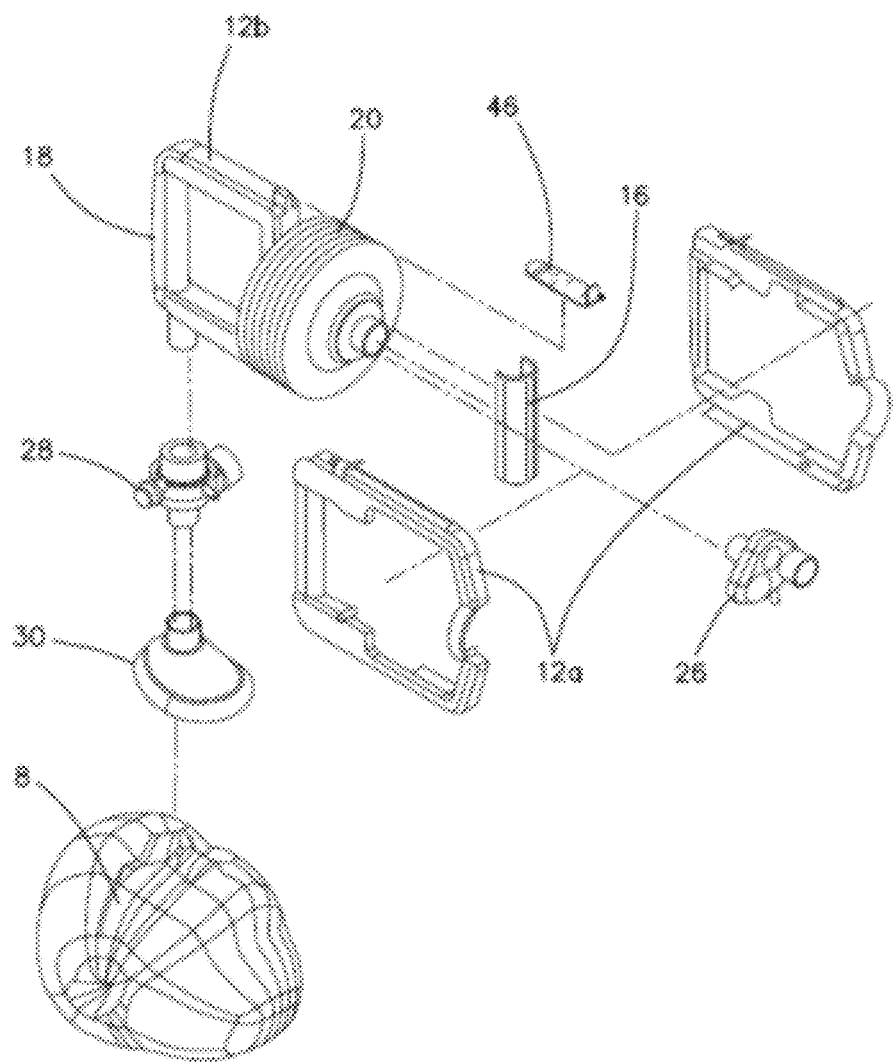
FIG. 4 is an exploded view of the resuscitation device seen in FIG. 1 when the patient is in the prone position.

The resuscitation device 10 also comprises a means to adjust the overall length of the bellows 20 which thereby changes the volume of air/oxygen delivered to the patient 8. For ease of description purposes, the term "distal" is meant to describe a component or portion thereof which is located away from where the head of the patient 8 is, while the term "proximal" refers to a component or portion thereof which is located closer to where the head of the patient 8 is. As best seen in FIGS. 3A and 3B, the distal edge of the moving frame 12A comprises a window or opening 44 defined within its surface which exposes a corresponding surface of the distal edge of the stationary frame 12B disposed there beneath. Disposed on the stationary frame 12B is a stop 38 which is sufficiently sized and shaped to protrude from the opening 44.

Figure 5:
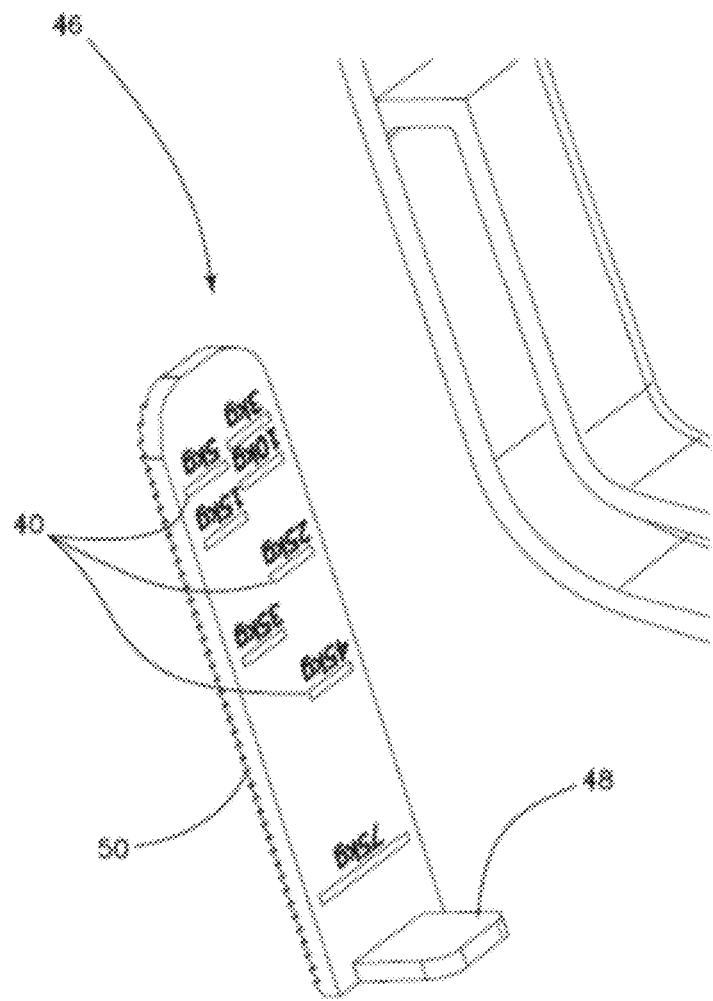
FIG. 5 is a magnified perspective view of the slide adjuster.

Also disposed between the stationary frame 12B and the moving frame 12A within the opening 44 is a slide adjuster 46 which can be seen in greater detail in FIG. 5. The slide adjuster 46 is substantially rectangular in shape and comprises a thumb tab 48 at one lateral end which provides the user with a surface to apply pressure against as is further detailed below. The slide adjuster 46 further comprises a plurality of teeth 50 disposed along its bottom surface and a plurality of measurement markings 40 disposed at specific points along its top surface. Each of the plurality of measurement markings 40 corresponds to an estimated weight of the patient 8 in kilograms. As seen in FIG. 5, the measurement markings 40 represent a corresponding plurality of pre-determined or pre-measured volumes of air that are contained within the bellows 20 when the device 10 is set to that specific corresponding measurement marking 40. In a preferred embodiment, each of the plurality of measurement markings 40 are labeled with a weight amount in kilograms which corresponds to the weight of the patient 8. For example, the first of the plurality of marked lines relative to the top surface of the slide adjuster 46 comprises a "3 kg" label, while a second marked line located vertically downward from the first marked line comprises a "5 kg" label and so on for each of the plurality of marked lines with each subsequent marked line comprising a larger and larger weight value until the final measurement marking 40 comprises a "75 kg" label. While FIG. 5 shows the measurement markings 40 comprising labels ranging from "3 kg" to "75 kg," this is meant to be for illustrative purposes only. Additional or different weight values or types of measurements may also be used without departing from the original spirit and scope of the invention. For example, the slide adjuster 46 may comprise an additional measurement marking 40 corresponding to a "105 kg" patient 8, which may be equivalently labeled as "230 lbs." or the like. Alternatively, the measurement markings 40 may be labeled by the volume of air which is delivered to the patient 8 when the device is set to that specific setting instead of by the patient's weight. In one embodiment best seen in FIGS. 3A and 3B, the labeling associated with each of the measurement markings 40 is reversed relative to the orientation of the patient 8 which helps the medical professional who is typically leaning over the patient 8 during treatment to quickly read and know what tidal volume the device 10 is currently set for.

Figure 7A:
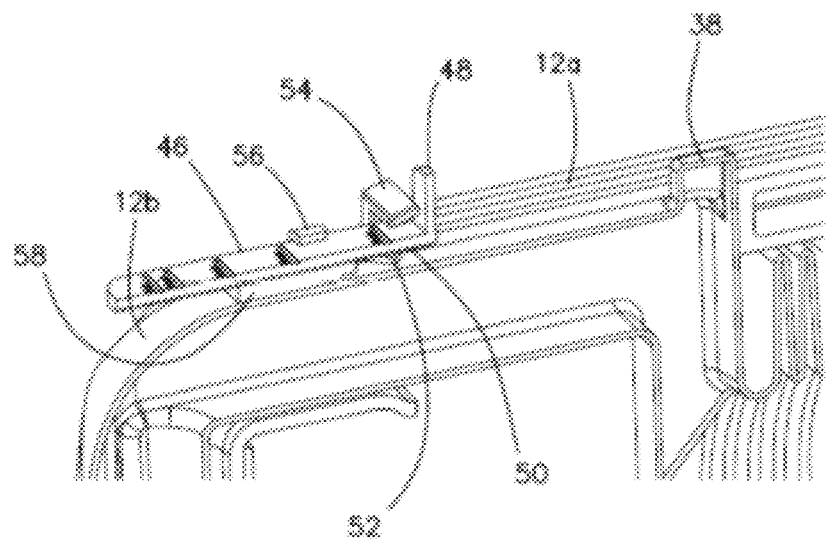
FIG. 7A is a magnified cross-sectional perspective view of the slide adjuster interacting with the moving and stationary frames of the resuscitation device.
Figure 7B:
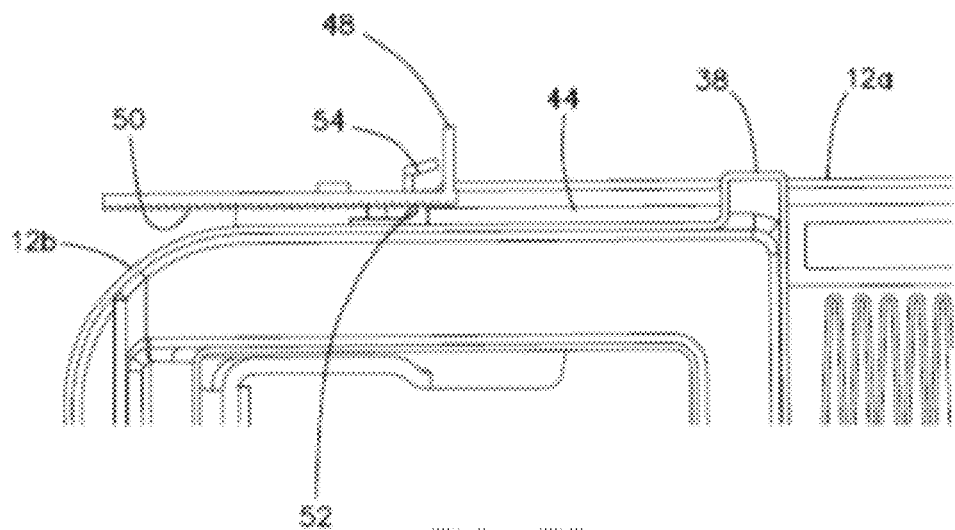
FIG. 7B is a magnified cross-sectional side view of the slide adjuster interacting with the moving and stationary frames of the resuscitation device.

Greater detail of how the slide adjuster 46 interacts with the stationary frame 12B and the moving frame 12A may be seen in FIGS. 7A and 7B. In the cross-sectional views of FIGS. 7A and 7B, the slide adjuster 46 is disposed on top of a raised surface 58 which forms part of the moving frame 12A. The raised surface 58 itself comprises a curved selector 56 which not only prevents any lateral movement of the slide adjuster 46 relative to the moving frame 12A, but also clearly marks the current tidal volume that the device 10 is set to deliver to a patient. Coupled to the raised surface 58 is a lock 52 which is further coupled to a lever 54. The lock 52 interacts with the plurality of teeth 50 of the slide adjuster 46 such that when pressure is applied to the thumb tab 48 in the distal direction, the slide adjuster 46 is permitted to move over the lock 52 in the distal direction only. When the thumb tab 48 is released, any reverse movement back in the proximal direction by the slide adjuster 46 is prevented due to the specific shape of the lock 52 which is specifically configured to fit in between each of the plurality of teeth 50 on the slide adjuster 46. To move the slide adjuster 46 back in the proximal direction, the lever 54 is depressed by the user which moves the lock 52 off of the teeth 50 disposed on the bottom surface of the slide adjuster 46, thereby permitting the user to move the slide adjuster 46 in either longitudinal direction relative to the moving frame 12A. When the lever 54 is released or otherwise allowed to return to its original position, the lock 52 moves upward against the bottom surface of the slide adjuster 46, specifically between two of the plurality of teeth 50 which locks the slide adjuster 46 into place relative to the moving frame 12A.

To use the resuscitation device 10, the user visually inspects the patient 8 and makes an estimation of their total body weight based on their appearance and their apparent height. The user then adjusts the size of the tidal volume to be delivered by adjusting the longitudinal position of the slide adjuster 46 relative to the moving frame 12A of the device 10. The user adjusts the relative longitudinal position of the slide adjuster 46 by applying pressure to the thumb tab 48 and pushing on the thumb tab 48 in the distal direction away from the patient 8 until the desired measurement marking 40 is now disposed under the selector 56. To readjust the slide adjuster 46 and move back in the proximal direction, the user actuates the lever 54 which moves the lock 52 off the teeth 50, thereby permitting the user to push the thumb tab 48 back in the proximal direction. When the user then stops actuating the lever 54, the lock 52 is then reinserted into the plurality of teeth 50 and holds the slide adjuster 46 in a new stationary position.

Figure 6:
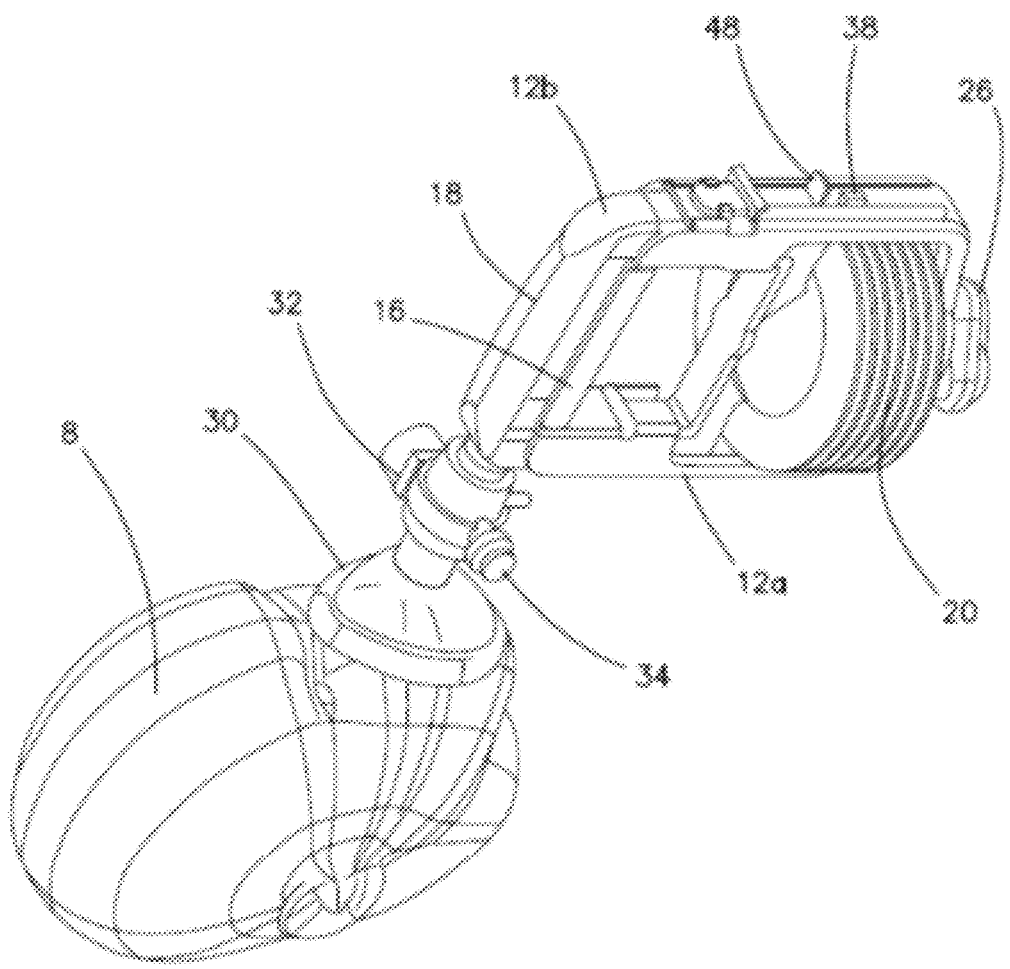
FIG. 6 is a perspective view of the resuscitation device seen in FIG. 1.

After adjusting the tidal volume of the device 10, the user may connect an oxygen supply to the oxygen valve 26 before approaching the patient 8 and placing the face mask 30 of the device 10 over the nose and mouth of the patient 8 as seen in FIG. 6. The oxygen source is coupled to the oxygen valve 26 by connecting a tube or other aperture to the oxygen inlet 66. Alternatively, the user can forego connecting an oxygen supply to the oxygen valve 26 and instead leave the device 10 to be used with ambient air/oxygen.

To illustrate, if the user approaches the patient 8 and determines that they weigh approximately 45 kg but the slide adjuster 46 is currently set for a patient weighing 75 kg, the user moves the slide adjuster 46 in the distal direction through the opening 44 of the moving frame 12A by applying pressure to the thumb tab 48 until the measurement marking 40 corresponding to "45 kg" is disposed beneath the selector 56. Because the lock 52 is in continuous contact with the teeth 50 whenever the slide adjuster 46 moves in the distal direction, the slide adjuster 46 is locked at the position appropriate for a 45 kg patient. The user may readjust the slide adjuster 46 as needed in case the user originally estimated the weight of the patient incorrectly or where multiple patients are to be treated using the same device 10. Additionally, if the user determines that the patient 8 weighs roughly 65 kg but the closest measurement markings 40 on the slide adjuster 46 are for "75 kg" and "45 kg," the user may interpolate where the "65 kg" measurement marking would be on the slide adjuster 46 and then slide it until the estimated "65 kg" position is disposed underneath the selector 56.

After the resuscitation device 10 has been properly adjusted to the specific size of the patient 8, the device 10 is ready to begin delivering tidal breaths to the patient 8. As seen in FIGS. 6, 9A, and 9B, the patient 8 is lying in the prone position with the face mask 30 placed over their nose and mouth with the resuscitation device 10 disposed parallel to the patient's body. When an airway adjunct such as an endotracheal tube is utilized in lieu of a mask, the procedure is substantially the same except that the patient valve 28 is attached to the adjunct instead of the mask 30. As best seen in the magnified view of FIG. 8A, because of the spring force associated with the bellows 20, the moving frame 12A is held in place against the stationary frame 12B with the thumb tab 48 resting against the stop 38. Because the slide adjuster 46 is prevented from moving laterally through the opening 44 by the stop 38 and is firmly held in place relative to the moving frame 12A via the lock 52, the moving frame 12A is initially held in a static position relative to the stationary frame 12B.

To provide a compression stroke, the user first places the palm of their hand against the handle 18 with their fingers wrapped around the traverse 16. The user then squeezes their fingers toward their palm which brings the traverse 16 and moving frame 12A toward the handle 18. Because the bellows 20 is coupled to both the moving frame 12A and the stationary frame 12B, the bellows 20 is compressed or contracted as seen in FIG. 9B as the moving frame 12A moves longitudinally in the proximal direction relative to the stationary frame 12B. Oxygen contained within the bellows 20 is forced out of the bellows 20 through the top portion 22 and into the hollow structure or volume of the stationary frame 12B. As the bellows 20 continues to be compressed, the oxygen continues flowing through the stationary frame 12B until it passes through the patient valve 28 and then finally to the patient 8 via the face mask 30 or other airway adjunct. The user continues to squeeze the traverse 16 towards the handle 18 until the concave surface of the traverse 16 meets the substantially cylindrical shape of the handle 18.

Figure 8A:
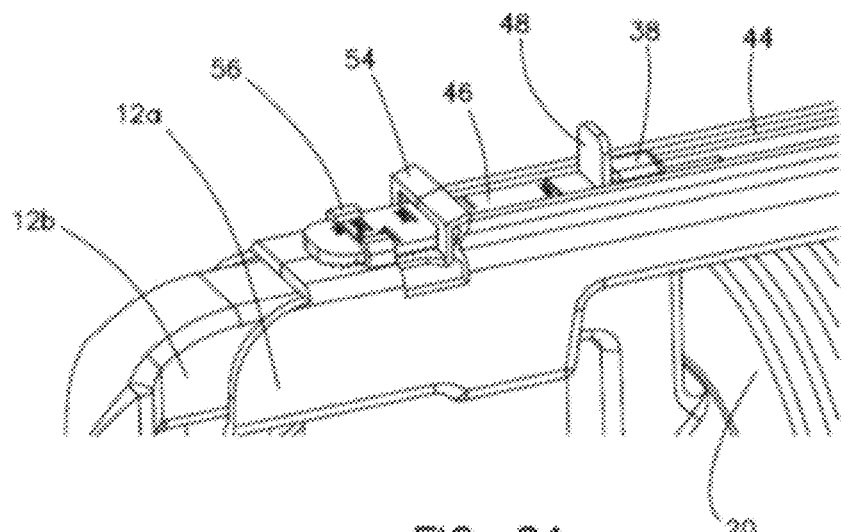
FIG. 8A is a magnified perspective view of the slide adjuster interacting with the moving and stationary frames of the resuscitation device at the beginning of a compression stroke.
Figure 8B:
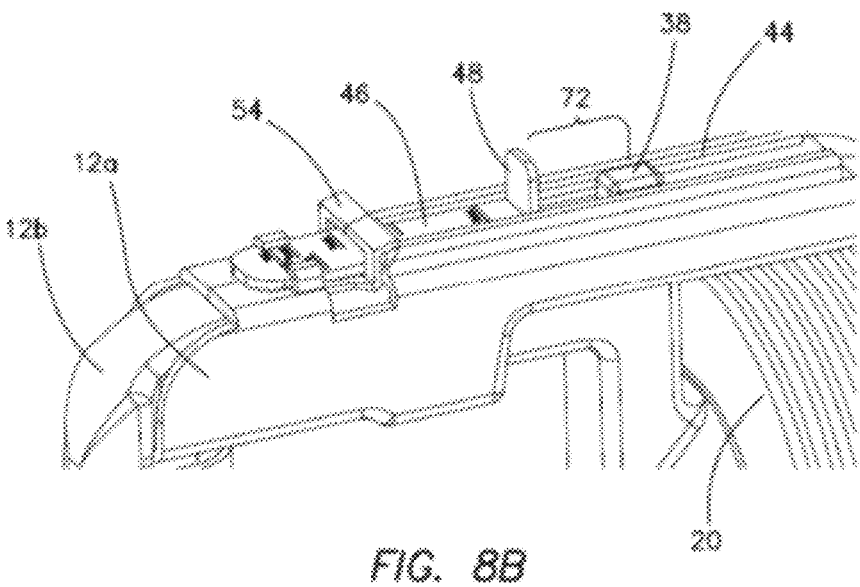
FIG. 8B is a magnified side view of the slide adjuster interacting with the moving and stationary frames of the resuscitation device at the end of a compression stroke.
Figure 9A:
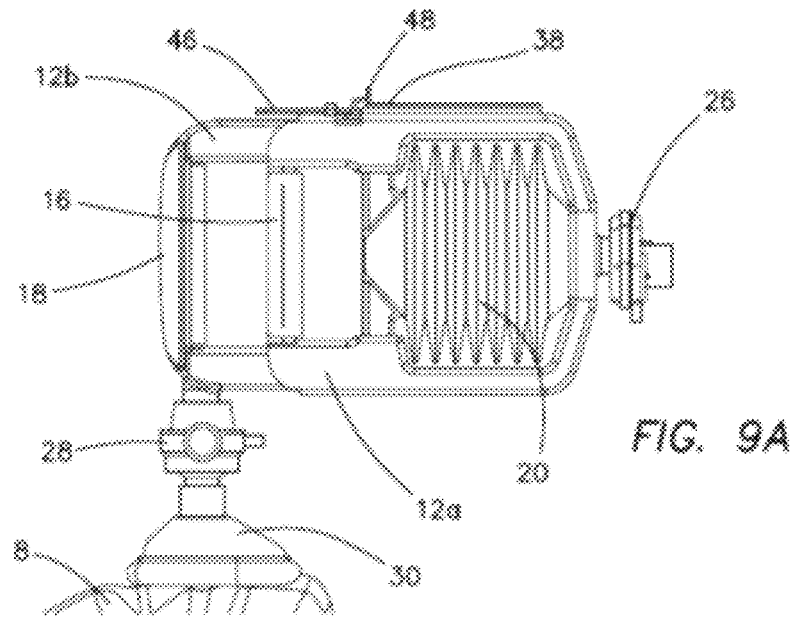
FIG. 9A is a side view of the resuscitation device being used on a patient in the prone position. The resuscitation device is seen as being at the beginning of a compression stroke with the bellows of the resuscitation device being in an expanded state.
Figure 9B:
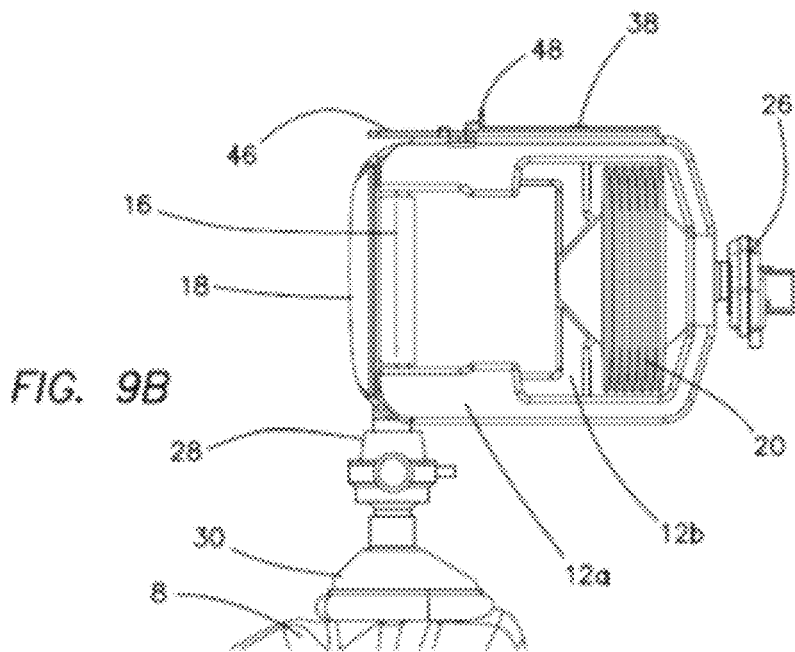
FIG. 9B is a side view of the resuscitation device being used on a patient in the prone position. The resuscitation device is seen as being at the end of a compression stroke with the bellows of the resuscitation device being in a compressed state.

A magnified view of the movement of the moving frame 12A and the slide adjuster 46 during the compression stroke can be seen in FIGS. 8A and 8B. FIG. 8A shows the moving frame 12 and slide adjuster 46 at the beginning of the compression stroke before the user has begun squeezing the traverse 16 and handle 18 together with the thumb tab 48 resting in a static position against the stop 38 of the stationary frame 12B. As seen in the figure, the slide adjuster 46 is set to deliver a tidal breath appropriate for a person weighing "25 kg." As the user begins squeezing the traverse 16 against the handle 18, the moving frame 12A begins to move proximally relative to the stationary frame 12B which remains in a static position. Because the slide adjuster 46 is firmly locked in place to the moving frame 12A, the thumb tab 48 moves proximally through the opening 44 off of and away from the stop 38. The thumb tab 48 continues to move away from the stop 38, thereby creating a distance 72 between the thumb tab 48 and the stop 38, until the traverse 16 of the moving frame 12A contacts the handle 18.

After the air/oxygen has been delivered to the patient 8 during the compression stroke, an intake stroke to refill the bellows 20 with air/oxygen is then initiated by the user relaxing their grip on the traverse 16. The spring force of the bellows 20 then pulls the moving frame 12A back in the distal direction away from the handle 18 while the stationary frame 12B continues to remain in a static position. Because the bellows 20 is coupled to both the moving frame 12A and the stationary frame 12B, the bellows 20 is expanded as seen in FIG. 9A as the moving frame 12A moves longitudinally in the distal direction relative to the stationary frame 12B. Incoming oxygen from the oxygen valve 26 is drawn into the bellows 20 through the bellows outlet 36.

As the bellows 20 continues to expand and the moving frame 12A continues to move in the longitudinal direction, the slide adjuster 46 and thumb tab 48 also move distally relative to the stationary frame 12B. The moving frame 12A continues move away from the handle 18 until the thumb tab 48 of the slide adjuster 46 makes contact with the stop 38 as seen in the magnified view of FIG. 8A. Because contact with the stop 38 halts all distal movement of the moving frame 12A, the expansion of the bellows 20 stops the moment the thumb tab 48 touches the stop 38 which thereby effectively limits the volume of oxygen which is permitted to enter the bellows 20 from the oxygen valve 26. For example, since it has been found that 6-8 ml of air/oxygen per kilogram is ideal for a patient, when the device 10 is set at the "75 kg" measurement marking 40, the bellows 20 will contain a tidal volume of 450-600 ml of air/oxygen. Conversely, when the device is set at the "3 kg" measurement marking 40, the bellows 20 will only contain a tidal volume of 18-24 ml of air/oxygen. Furthermore, because contact between the stop 38 and the thumb tab 48 ends the intake stroke of the resuscitation device 10, it is physically impossible for the user to over ventilate the patient 8 no matter how much force they may apply to the traverse 16 and handle 18. The resuscitation device 10 may then be actuated again as many times as is required by the user squeezing the traverse 16 of the moving frame 12A towards the handle 18 which then initiates a new compression stroke and delivers the air/oxygen from the resupplied bellows 20. At the end of each compression stroke, the bellows 20 is allowed to refill with a volume of oxygen as dictated by the position of the slide adjuster 46 and thumb tab 48 relative to the opening 44 of the moving frame 12A. The user may repeatedly actuate the resuscitation device 10 for as long as treatment is required. When the patient 8 no longer requires air/oxygen, the resuscitation device 10 is removed from the patient 8 by simply lifting the face mask 30 off of the patient's nose and mouth.

It is understood that by manipulating the slide adjuster 46, the resuscitation device 10 is able to provide the ideal tidal breath for every patient, regardless of their relative size. By manipulating the slide adjuster 46 to the desired measurement marking 40, the effective length that the slide adjuster 46 which extends into the opening 44 is adjusted. The length of the slide adjuster 46 which extends into the opening in turn dictates the volume of oxygen which is allowed to enter the bellows 20 during the intake stroke. Specifically, the larger the patient 8, the shorter the slide adjuster 46 and thumb tab 48 extend into the opening 44 which effectively extends the amount of time that air/oxygen permitted to enter the bellows 20 during the intake stroke. In contrast for a small patient 8, the slide adjuster 46 and thumb tab 48 extend a significantly longer length into the opening 44 than that for a larger patient 8, thereby limiting the time the oxygen may inflate the bellows 20 which in turn limits the volume of oxygen available to be delivered to the patient 8 during the next compression stroke.

Figure 10A:
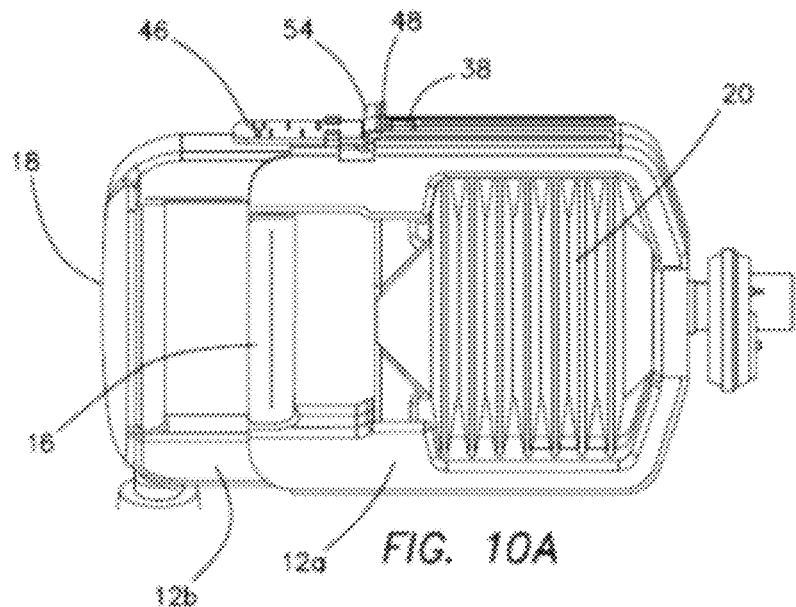
FIG. 10A is a perspective view of the resuscitation device at the beginning of a compression stroke when the slide adjuster has been set to deliver a tidal breath for a large patient.
Figure 10B:
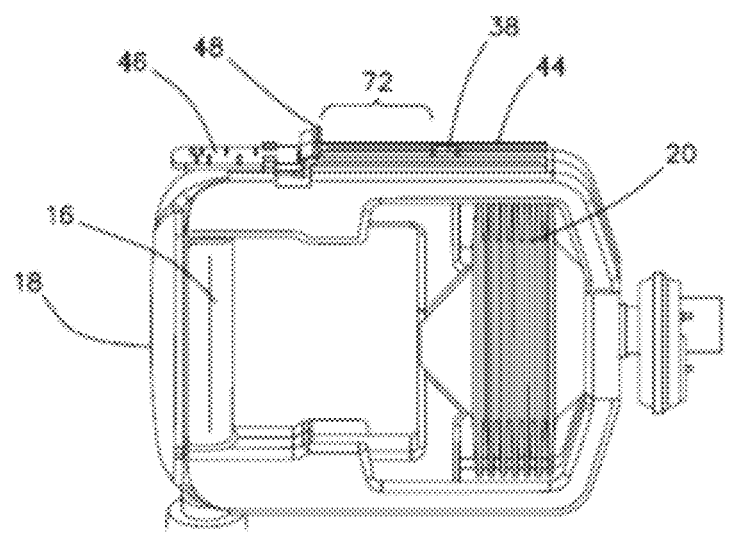
FIG. 10B is a perspective view of the resuscitation device at the end of a compression stroke when the slide adjuster has been set to deliver a tidal breath for a large patient.
Figure 11A:
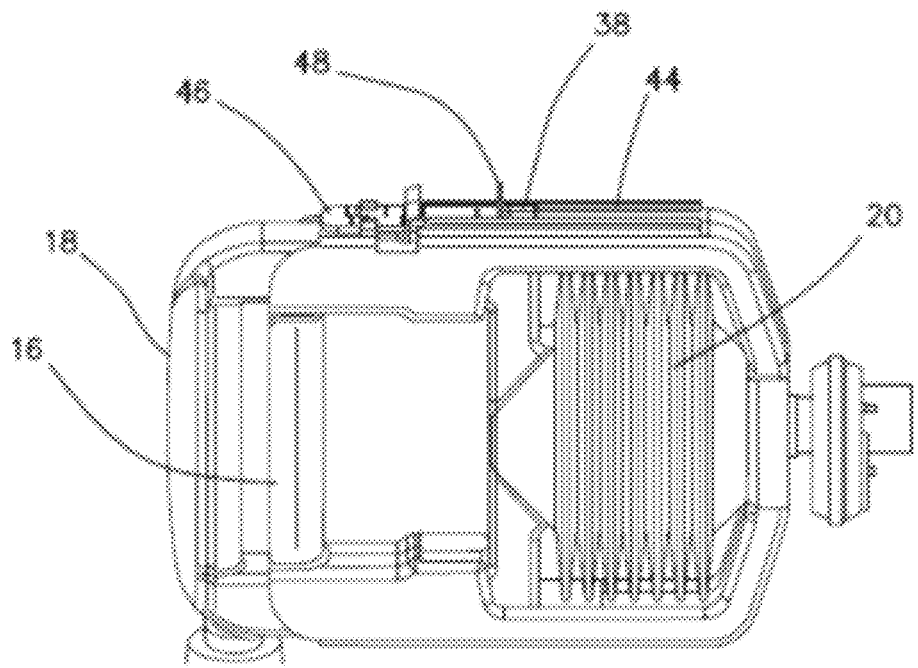
FIG. 11A is a perspective view of the resuscitation device at the beginning of a compression stroke when the slide adjuster has been set to deliver a tidal breath for a small patient.
Figure 11B:
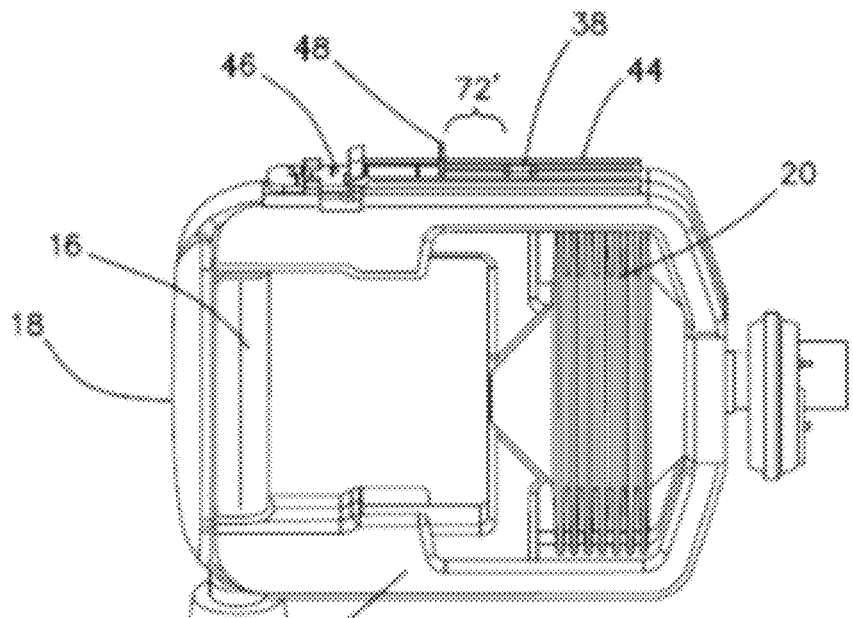
FIG. 11B is a perspective view of the resuscitation device at the end of a compression stroke when the slide adjuster has been set to deliver a tidal breath for a small patient.

An illustration of using the resuscitation device 10 for both a large patient and a small patient can be seen in FIGS. 10A-10B and 11A-11B, respectively. In FIG. 10A, the slide adjuster 46 has been set for the resuscitation device 10 to deliver tidal breaths to a large patient at the start of the compression stroke. Specifically, the slide adjuster 46 has been fixed relative to the moving frame 12A so that the lever 54 is disposed over the most distally located measurement marker 40. At the end of the compression stroke seen in FIG. 10B, the proximal portion of the slide adjuster 46 can be seen extending over the proximal end of the moving frame 12A while the thumb tab 48 has been a moved a set distance 72 from the stop 38. In contrast, in FIG. 11A the slide adjuster 46 has been set to deliver tidal breaths to a small patient at the start of the compression stroke. Specifically, the slide adjuster 46 has been fixed relative to the moving frame 12A so that the lever 54 is disposed over a more proximally located measurement marker 40 than what is seen in FIGS. 10A and 10B. At the end of the compression stroke seen in FIG. 11B, the thumb tab 48 has moved a set distance 72' from the stop 38. As can be seen in FIGS. 10B and 11B, the distance 72 that the thumb tab 48 has moved during the compression stroke for a large patient is significantly larger than the distance 72' that the thumb tab 48 has moved for a small patient. It is therefore easily understood that because the moving frame 12A is more restricted in its movement during the intake stroke for a smaller patient than it is for a larger patient, the amount of oxygen being drawn into the bellows 20 for a smaller patient is in turn smaller than it is for a larger patient.

Figure 19:
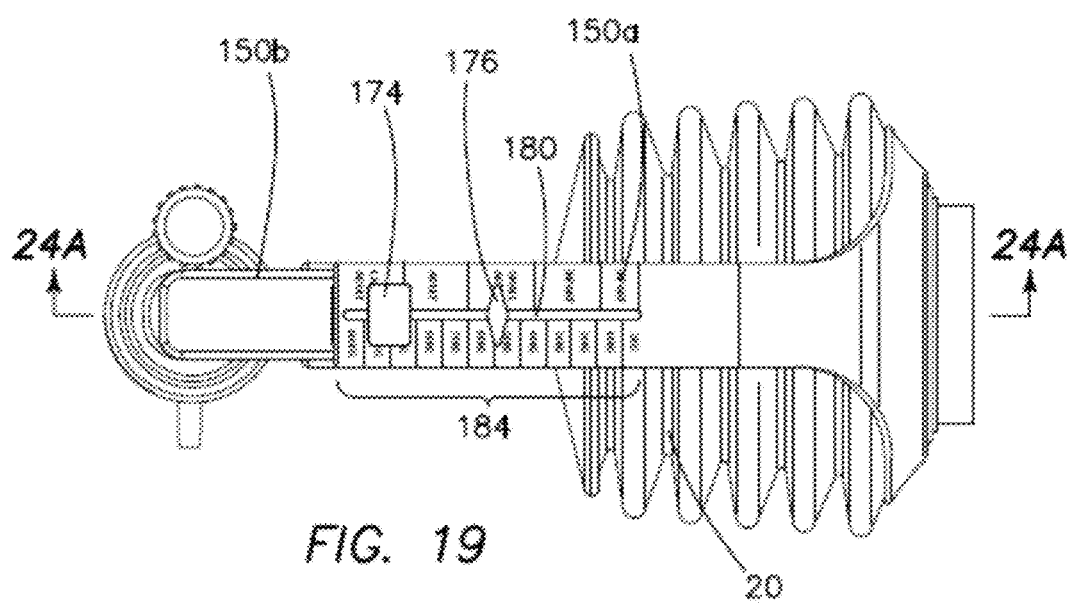
FIG. 19 is a top down perspective view showing the top of the moving frame and a measurement table disposed thereon.
Figure 20:
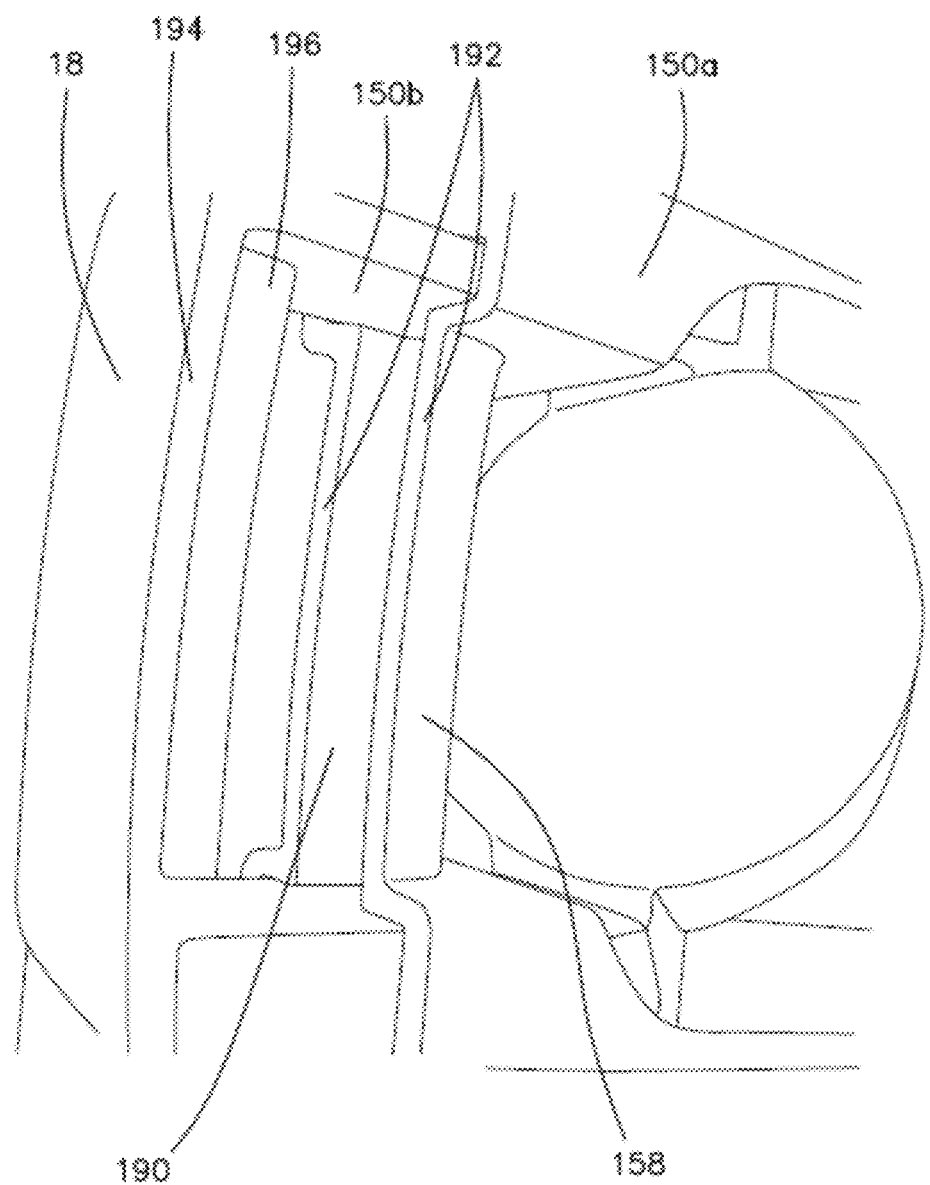
FIG. 20 is a magnified perspective view of the proximal end of the alternative embodiment of the resuscitation device showing the handle of the stationary frame and the concave interior of the traverse of the moving frame.
Figure 21:
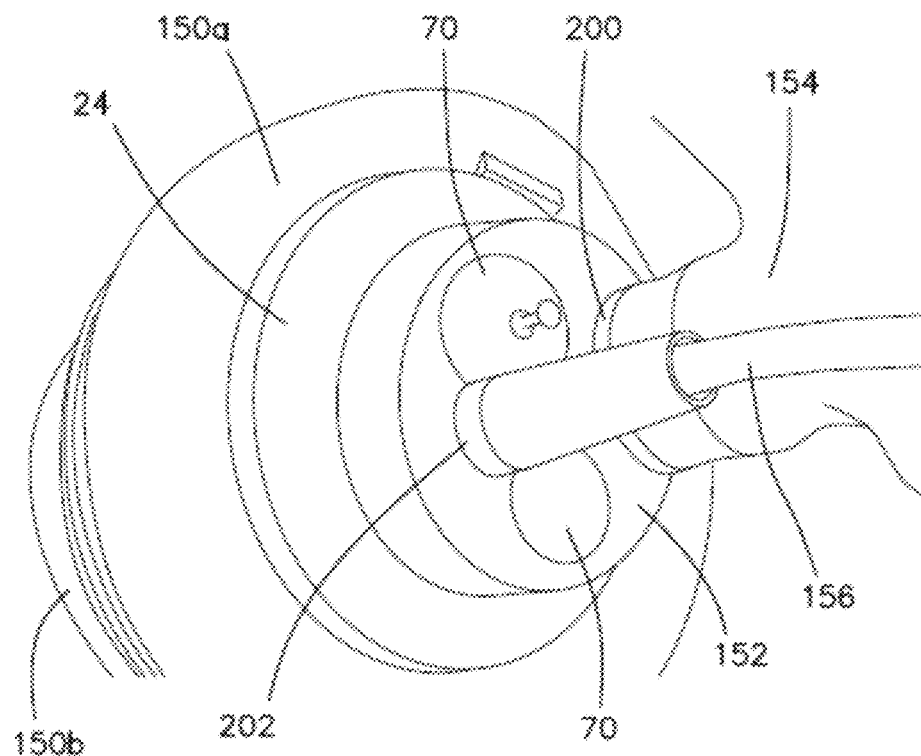
FIG. 21 is a magnified perspective view of the distal end of the alternative embodiment of the resuscitation device showing the oxygen valve incorporated into the bellows of the device.

A related embodiment of the resuscitation device may be seen in FIGS. 17-24B and is denoted generally by reference numeral 10'. The resuscitation device 10' comprises a substantially U-shaped frame 150 which itself comprises a moving frame 150a and a stationary frame 150b. Disposed across one lateral side of the moving frame 150a is an ergonomic traverse 158 which is contoured to accommodate the hand and fingers of a user, for example an EMT or other medical professional. Disposed across a lateral edge of the stationary frame 150b in turn is an ergonomic handle 18 that is configured and shaped to be gripped by the palm of the user. The moving frame 150a comprises a hollow interior volume 166 described in further detail below which accommodates the stationary frame 150b in a nested configuration therein as seen in FIGS. 17, 18, and 20-22. The hollow interior volume 166 of the moving frame 150a allows it to move over to the stationary frame 150b. Coupled to both the moving frame 150a and the stationary frame 150b is a flexible and extendable bellows 20. Specifically, a proximal portion 22 of the bellows 20 is incorporated into the stationary frame 150b so that the internal volume of the bellows 20 is in fluidic communication with in the internal hollow volume 166 of the stationary frame 150b as best seen in the cross sectional view of FIG. 24A. Similarly a distal portion 24 of the bellows 20 is incorporated into the moving frame 150a as best seen in FIG. 21 so that the internal volume of the bellows 20 is also in fluidic communication with an oxygen valve 152 coupled to the moving frame 150a. It can be seen therefore that the bellows 20 serves as a conduit for oxygen to flow from the oxygen valve 152 to the patient 8 in a series of predetermined tidal breaths as is described in further detail below.

The resuscitation device 10' further comprises a patient valve 28 which may be manipulated or adjusted to regulate the flow of air or oxygen there through as is known in the art. The patient valve 28 is in fluidic communication with the internal volume of the hollow interior of the stationary frame 150b. A face mask 30 is in turn removably coupled to the patient valve 28. The face mask 30 is sufficiently sized and shaped to fit comfortably over the nose and mouth of a patient 8 as seen in FIG. 1. The face mask 30 is further coupled to the patient valve 28 so that the face mask 30 may be rotated with respect to the patient valve 28 thereby allowing the resuscitation device 10' to be quickly and efficiently applied to the patient 8 regardless of the patient's initial orientation relative to the device 10'.

Figure 24B:
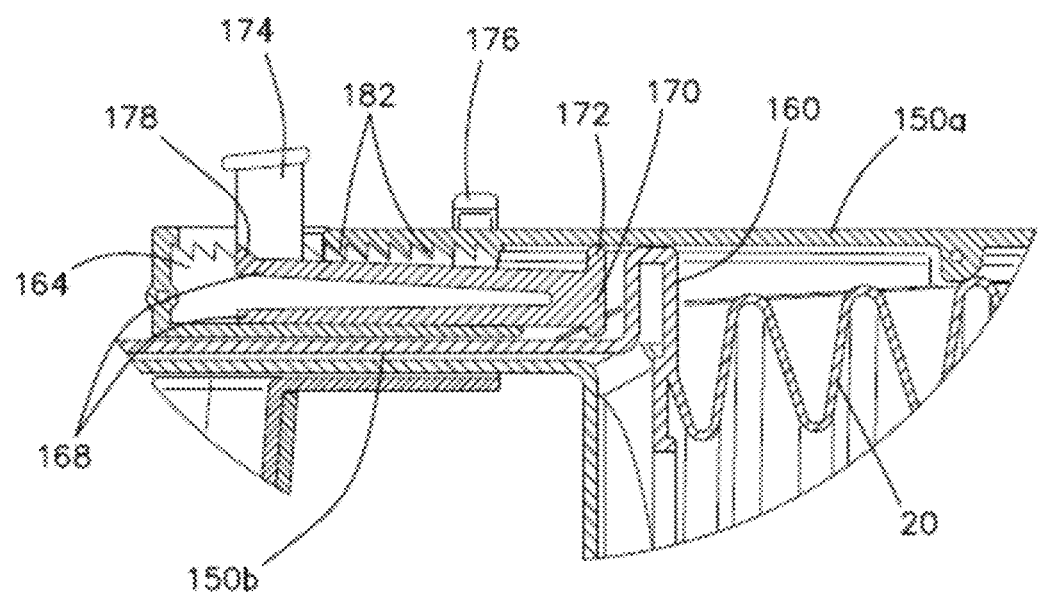
FIG. 24B is a magnified cross sectional view of the interaction between the slide selector, the moving frame, and the stationary frame seen in FIG. 24A.

The alternative embodiment of the resuscitation device 10' also comprises an alternative means to adjust the overall length of the bellows 20 which in turn changes the volume of air/oxygen delivered to the patient 8. As best seen in FIGS. 17A-18B and 24B, the distal edge of the stationary frame 150b comprises a stop 160 which is disposed perpendicularly or orthogonal relative to a lateral axis of the stationary frame 150b and the bellows 20. The moving frame 150a in turn comprises a slide selector 162 disposed within a cavity 164 defined within a portion of the moving frame 150a. The slide selector 162 extends out of the cavity 164 of the moving frame 150a so that a distal end of the slide selector 162 is disposed between an inner surface of the moving frame 150a and an outer surface of the stationary frame 150b as best seen in FIG. 24B.

Figure 23:
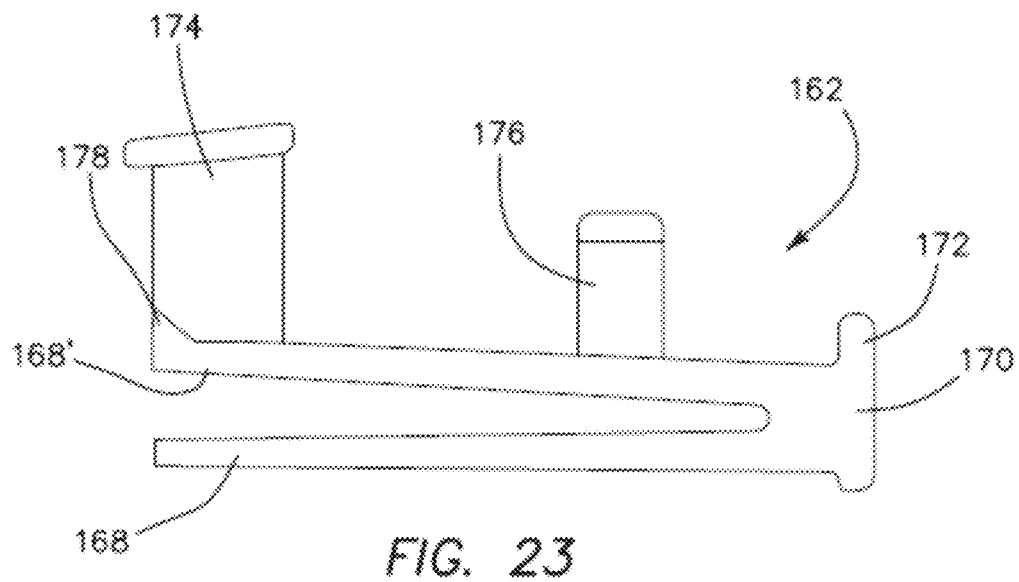
FIG. 23 is a magnified side view of the slide selector used in the alternative embodiment of the resuscitation device.
Figure 22:
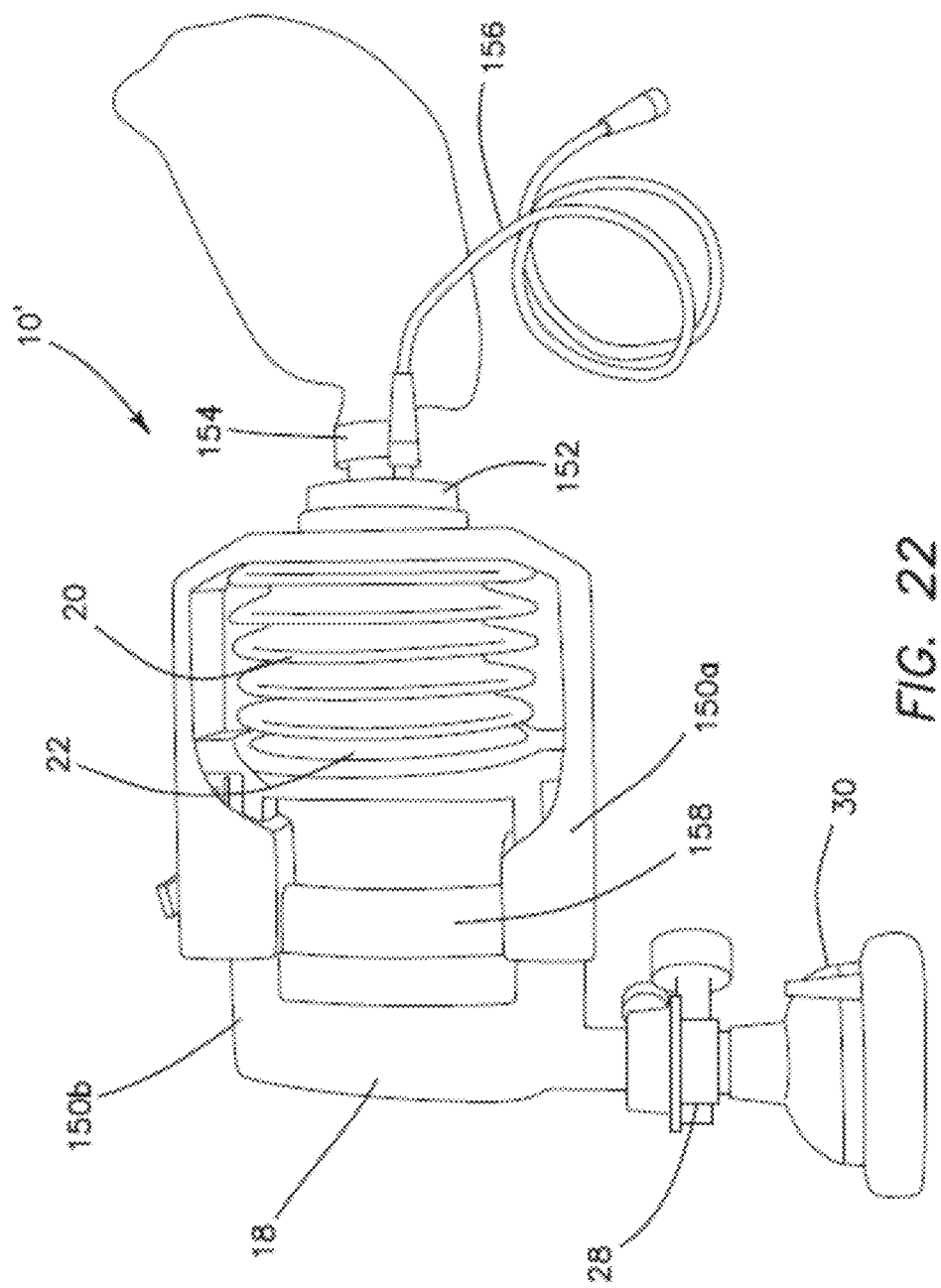
FIG. 22 is a side view of the alternative embodiment of the resuscitation device comprising a slide selector seen in FIGS. 17-21.

Greater detail of the slide selector 162 may be had by turning to FIG. 23. The slide selector 162 principally comprises a pair of flexible tines 168, 168' which are joined together to form a resilient spring such that either of the tines 168, 168' may be bent towards one another or otherwise squeezed together when an external force is applied and then allowed return to their initial positions when the external force is removed. The distal end of the slide selector 162 comprises a flat edge 170 with an extended lip 172. The slide selector 162 further comprises a thumb depress 174 disposed on the very proximal end of an upper tine 168'. Disposed midway down the length of the same upper tine 168' is a marker 176. Both the thumb depress 174 and the marker 176 extend in a substantially vertical direction relative to the tines 168, 168'. The marker 176 and the thumb depress 174 are specifically disposed in the center of the width portion of the upper tine 168'. The slide selector 162 further comprises a pawl 178 disposed at the very proximal end of the upper tine 168', the pawl 178 further being disposed on either lateral side of the thumb depress 174.

Figure 24A:
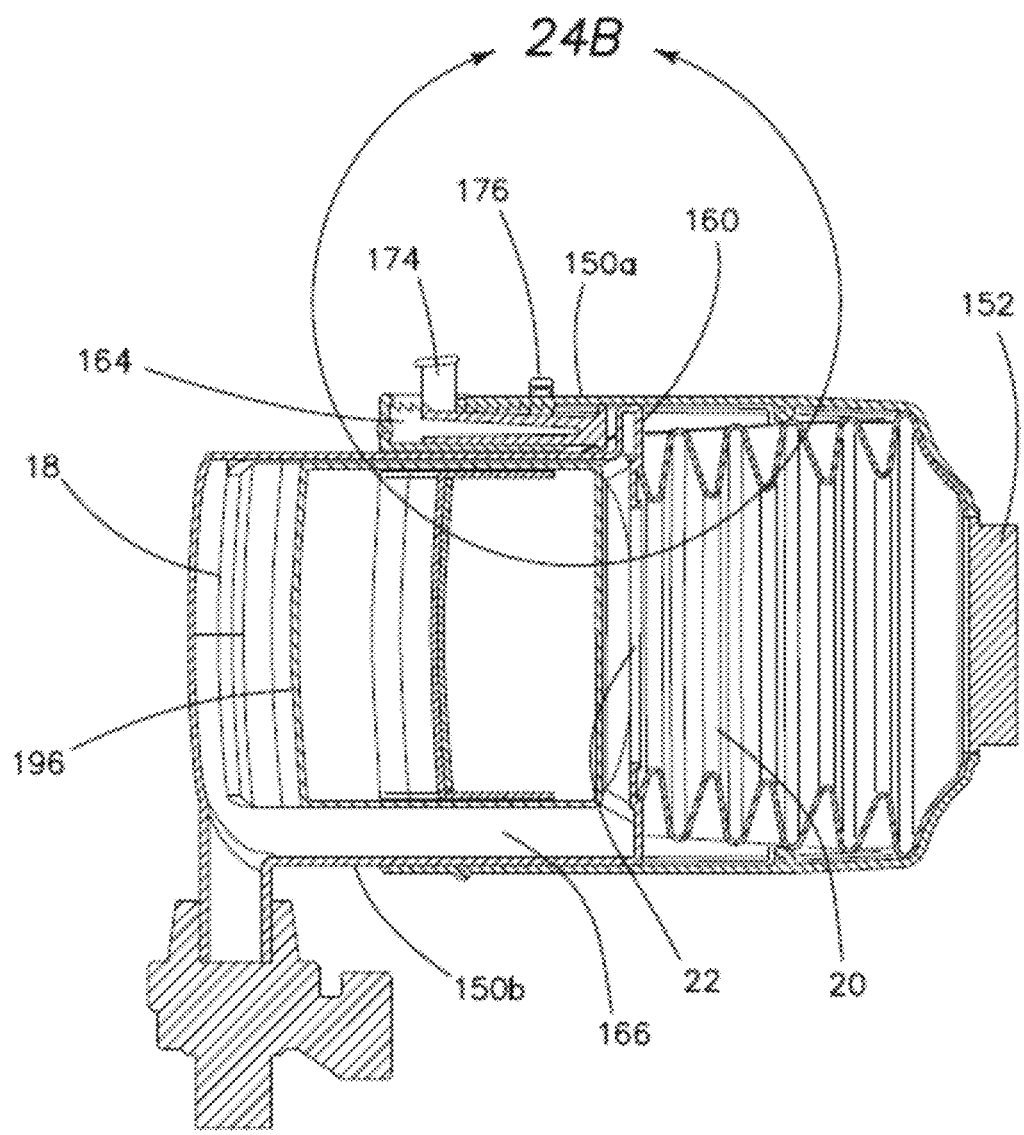
FIG. 24A is a side cross sectional view of the alternative embodiment of the resuscitation device seen in FIG. 22.

Operation of the slide selector 162 and how it interacts with the moving frame 150a and the stationary frame 150b may be had by briefing turning to FIGS. 24A and 24B. The underside or inner surface of the moving frame 150a comprises a plurality of teeth 182 disposed along its length. Therefore when the slide selector 162 is disposed in the cavity 164 of the moving frame 150a, the pawl 178 is disposed between at least two of the plurality of teeth 182. The pawl 178 and the teeth 182 are sufficiently sized and shaped so that all lateral movement of the slide selector 162 is prevented. To change the position of the slide selector 162 relative to the moving frame 150a, the user depresses or presses down upon the thumb depress 174 which bends the upper tine 168' and moves it downward toward the bottom tine 168, thereby taking out the pawl 178 from between at least two of the plurality of teeth 182. The user may then move the slide selector 162 in the distal direction by either pushing the thumb depress 174 in the distal direction, or more preferably, by squeezing the handle 18 and traverse 158 together, thereby moving the moving frame 150a back in the proximal direction relative to the stationary frame 150b. As the slide selector 162 moves relative to the moving frame 150a, the marker 176 moves through a narrow slit 180 defined in the moving frame 150a as best seen in FIG. 19. When the slide selector 162 has reached the desired position as detailed further below, the user releases the thumb depress 174 which allows the upper tine 168' to resiliently move back into its original position and reinsert the pawl 178 in between two teeth 182 at the new position of the slide selector 162. The user also releases their grip on the handle 18 and traverse 158, thereby permitting the bellows 20 to expand under its associated spring force which moves the moving frame 150a back in the distal direction until the flat edge 170 of the slide selector 162 makes contact with the stop 160 of the stationary frame 150b. To move the slide selector 162 in the proximal direction, the user again depresses or presses downward on the thumb depress 174 so that the pawl 178 is removed from the teeth 182. Next, while still pressing down on the thumb depress 174, the user relaxes their grip on the handle 18 and traverse 158, thereby allowing the bellows 20 to expand under its associated spring force. Because the stationary frame 150b is held in place by the user, the moving frame 150a is pushed in the distal direction by the spring force of the expanding bellows 20. The net result therefore is that the marker 176 moves proximally through the length of the slit 180. When the desired position is reached, the user then again releases the thumb depress 174 which brings the pawl 178 back into contact between the plurality of teeth 182, thereby locking the slide selector 162 into place at its new position. The bellows 20 is then permitted to expand until the stop 160 comes into contact with the flat edge 170 of the slide selector 162.

The moving frame 150a further comprises a measurement table 184 which itself comprises a plurality of measurement markings disposed at specific points along its surface. Each of the plurality of measurement markings within the measurement table 184 correspond to an estimated weight of the patient 8 in kilograms. As seen in FIG. 19, each of the markings in the measurement table 184 represent a corresponding plurality of pre-determined or pre-measured volumes of air that are contained within the bellows 20 when the device 10' is set to that specific corresponding measurement marking. In the embodiment seen in FIG. 19, one vertical side of the table 184 comprises a plurality of markings which are labeled with a rough or approximate age category of the patient 8 being treated. For example, at the distal end of the table 184, the marking corresponds to a proper tidal volume for a neonatal infant, while at the most proximal end of the table the marking corresponds to a proper tidal volume for a large adult. The opposing vertical side of the table 184 comprises a plurality of markings which represent a weight amount in kilograms which corresponds to the weight of the patient 8. For example, the first or most distal of the plurality of marked lines relative to the slide selector 162 comprises a "2 kg" label, while a second marked line located vertically downward from the first marked line comprises a "10 kg" label and so on for each of the plurality of marked lines with each subsequent marked line comprising a larger and larger weight value until the final measurement marking comprises a "90 kg" label. While FIG. 19 shows the measurement markings comprising labels ranging from "2 kg" to "90 kg," this is meant to be for illustrative purposes only. Additional or different weight values or types of measurements may also be used without departing from the original spirit and scope of the invention. For example, the table 184 may comprise an additional measurement marking corresponding to a "100 kg" or a "110 kg" patient 8, which may be equivalently labeled as "230 lbs." or the like. Alternatively, the measurement markings may be labeled by the volume of air which is delivered to the patient 8 when the device is set to that specific setting instead of by the patient's weight. In one embodiment best seen in FIG. 19, the labeling associated with each of the table 184 is reversed relative to the orientation of the patient 8 which helps the medical professional who is typically leaning over the patient 8 during treatment to quickly read and know what tidal volume the device 10 is currently set for.

Figure 17A:
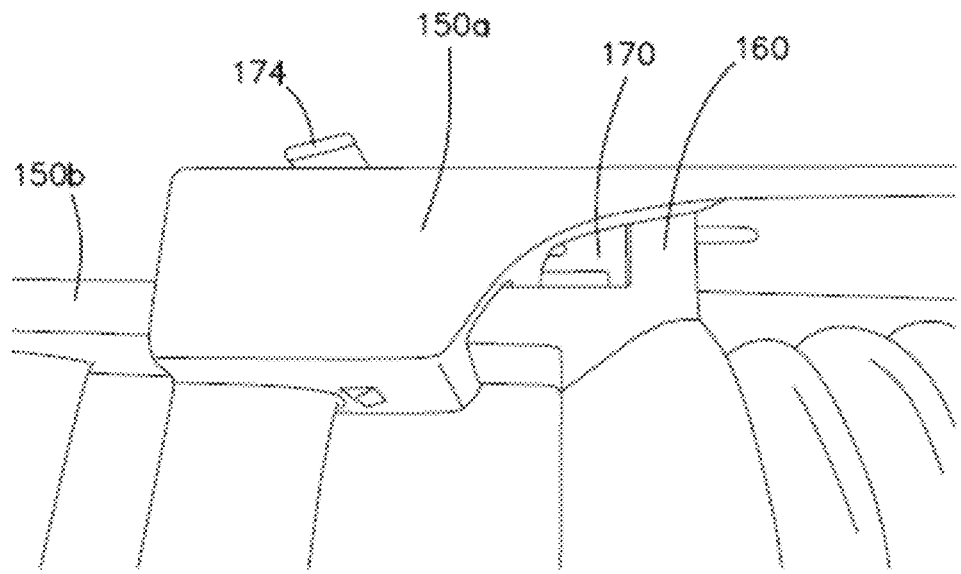
FIG. 17A is a magnified view of an alternative embodiment of the resuscitation device comprising a slide selector disposed between the moving frame and the stationary frame when the slide selector has been set to deliver a large tidal breath at the beginning of a compression stroke.
Figure 17B:
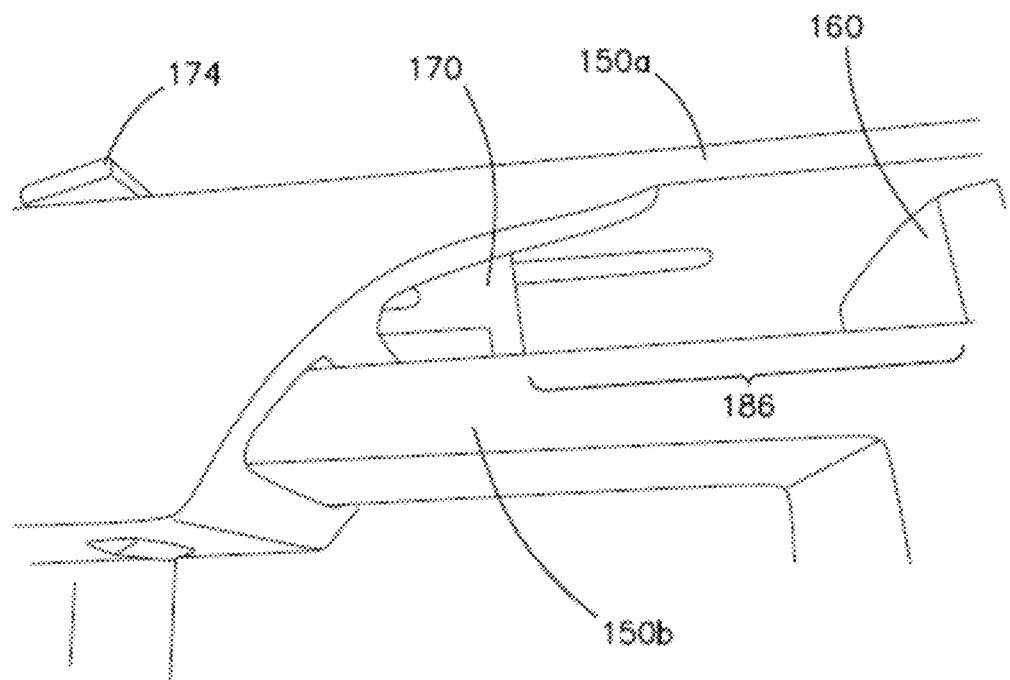
FIG. 17B is a magnified view of the alternative embodiment of the resuscitation device comprising a slide selector disposed between the moving frame and the stationary frame seen in FIG. 17A at the beginning of an intake stroke.
Figure 18A:
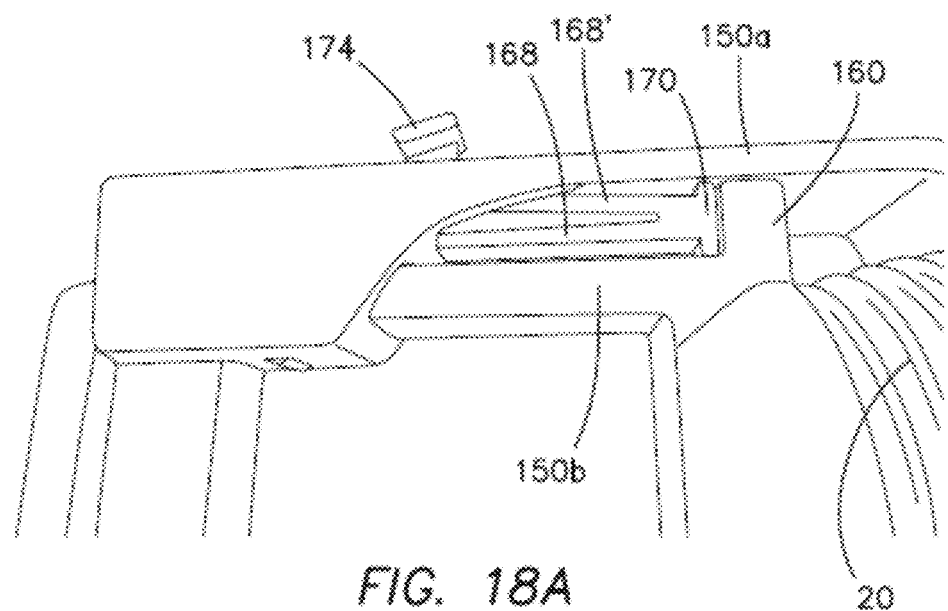
FIG. 18A is a magnified view of the alternative embodiment of the resuscitation device comprising a slide selector seen in FIG. 17A when the slide selector has been set to deliver a small tidal breath at the beginning of a compression stroke.
Figure 18B:
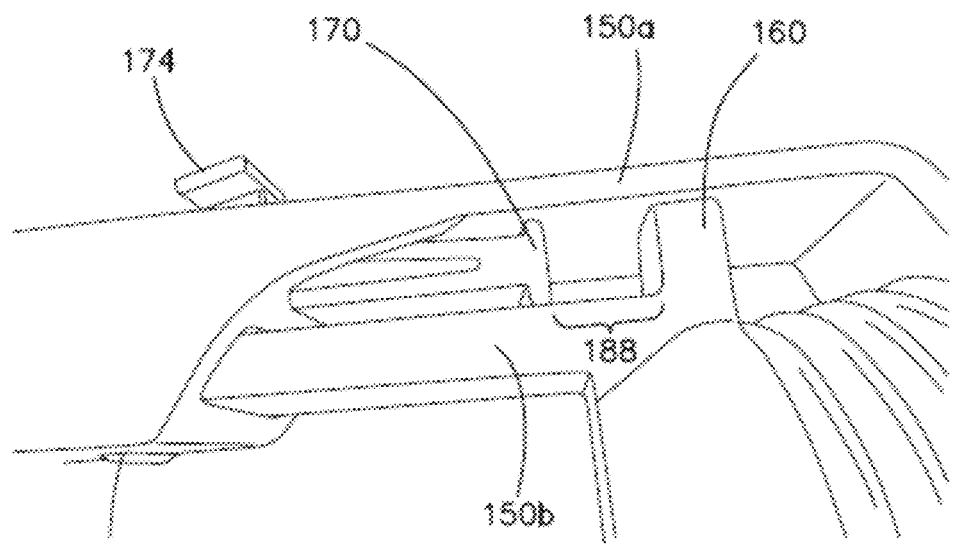
FIG. 18B is a magnified view of the alternative embodiment of the resuscitation device comprising a slide selector disposed between the moving frame and the stationary frame seen in FIG. 18A at the beginning of an intake stroke.

Similar to the prior embodiment discussed above, with the slide selector 162 properly set, air/oxygen may be delivered to the patient 8 through a series of compression and intake strokes. Greater detail of how the slide selector 162 of the current embodiment interacts with the stationary frame 105b and the moving frame 105a when the device 10' is in use may be seen in FIGS. 17A-18B. In FIG. 17A, the slide selector 162 has been set for the resuscitation device 10' to deliver tidal breaths to a large patient at the start of the compression stroke. Specifically, the flat edge 170 of the slide selector 162 has been fixed relative to the moving frame 150a so that the thumb depress 174 is disposed substantially at the proximal end of the moving frame 150a. At the end of the compression stroke seen in FIG. 17B, the flat edge 170 of the slide selector 162 can be seen having been a moved a set distance 186 from the stop 160. In contrast, in FIG. 18A the slide selector 162 has been set to deliver tidal breaths to a small patient at the start of the compression stroke. Specifically, the slide selector 162 has been fixed relative to the moving frame 105a so that the slide selector 162 extends further from the cavity 164 and over the stationary frame 150b than what is seen in FIGS. 17A and 17B. At the end of the compression stroke seen in FIG. 18B, the flat edge 170 of the slide selector 162 has moved a set distance 188 from the stop 160. As can be seen by comparing FIG. 17B with FIG. 18B, the distance 186 that the slide selector 162 has moved during the compression stroke for a large patient is significantly larger than the distance 188 that the slide selector 162 has moved for a small patient. It is therefore easily understood that because the moving frame 150a is more restricted in its movement during the intake stroke for a smaller patient than it is for a larger patient, the amount of oxygen being drawn into the bellows 20 for a smaller patient is in turn smaller than it is for a larger patient.

Greater detail of how the handle 18 interacts with the traverse 158 may be seen in FIG. 20. The traverse 158 comprises a substantially U-shaped cross section which thereby defines a concave interior 190 throughout the vertical height of the traverse 158. The concave interior 190 also comprises a pair of flat, vertical edges 192 disposed on either side of the traverse 158. The concave interior 190 is sufficiently sized and shaped to accommodate a substantially rectangular shaped protrusion 196 disposed along the vertical height of the handle 18 during a compression stroke. Specifically, as the user squeezes the traverse 158 towards the handle 18 in order to deliver a patient-specific volume of oxygen to the patient 8, the moving frame 150*a* moves proximally over the stationary frame 150*b* and brings the concave interior 190 over the protrusion 196. The user may continue to squeeze the traverse 158 until the vertical edges 192 make contact with a corresponding pair of flat surfaces 194 disposed on either side of the protrusion 196, thereby stopping the relative movement between the moving frame 150*a* and the stationary frame 150*b* and preventing the over inflation of the lungs of the patient 8. During the intake stroke, the user relaxes their grip on the handle 18 and traverse 158 which moves the moving frame 150*a* back in the distal direction which in turn moves the vertical edges 192 of the traverse 158 off of the flat surfaces 194 and exposes the protrusion 196.

The distal end of the bellows 20 and the resuscitation device 10' generally may be seen in FIG. 21. As seen, the oxygen valve 124 is integrated into the distal portion of the bellows 20 and is fluidly communicated with its internal volume. Similar to the oxygen valve 24 of the previous embodiment, the oxygen valve 152 here comprises a plurality of valves 70 which are used to regulate the volume and pressure of the oxygen entering the bellows 20 via the valves 70. The oxygen valve 152 may be manipulated by either the medical professional at the time of use or alternatively, at the point of manufacture to regulate the volume and pressure of the oxygen entering the bellows 20 via the valves 70. The oxygen valve 152 further allows excess oxygen to bleed off or otherwise be expelled from the device 10' if the pressure within the bellows 20, patient valve 28, and/or oxygen valve 152 has exceeded a predetermined threshold value. As also seen in FIG. 21, the oxygen valve 152 further comprises means to couple both a resuscitation bag 154 and an oxygen tube 156 to the resuscitation device 10' via a bag connector 200 and a tube connector 202, respectively.

Figure 14:
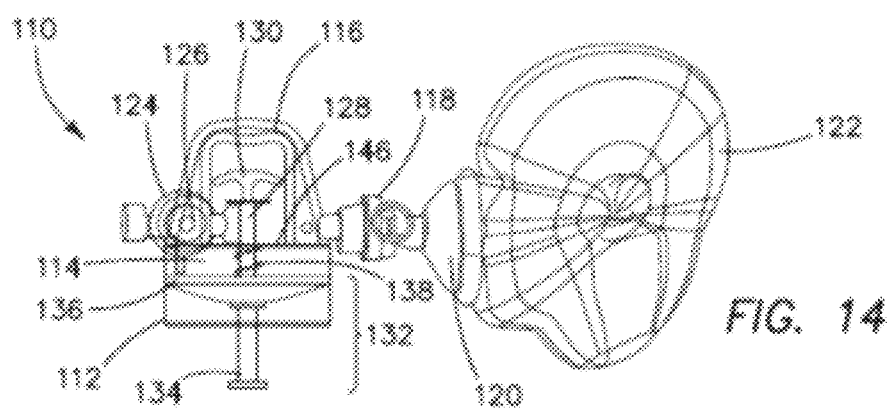
FIG. 14 is a side view of an alternative embodiment of the resuscitation device comprising a spring actuated diaphragm.

An alternative embodiment of the current invention is seen in FIG. 14 and is denoted generally by reference numeral 110. The resuscitation device 110 comprises a substantially cylindrical housing 112 which itself comprises an internal volume 114. Coupled to the top surface 146 of the housing is a handle 116 which substantially comprises an inverted U-shape and is contoured to accommodate the hand and fingers of a user, for example an EMT or other medical professional. Coupled to the resuscitation device 110 and communicated to the internal volume 114 is a patient valve 118 which may be manipulated or adjusted to regulate the flow of air or oxygen there through as is known in the art. A face mask 120 is in turn removably coupled to the patient valve 118. The face mask 120 is sufficiently sized and shaped to fit comfortably over the nose and mouth of a patient 122 as seen in FIG. 14.

Also coupled to the resuscitation device 110 is an oxygen valve 124 which is configured to be coupled to an oxygen tank or other oxygen source, either directly or indirectly through tubing. The oxygen valve 124 is communicated to the internal volume 114 of the housing 112 via an oxygen inlet 126. The oxygen valve 124 further allows excess oxygen to bleed off or otherwise be expelled from the device 110 if the pressure within the internal volume 114 has exceeded a predetermined threshold value.

The resuscitation device 110 also comprises a hollow central rod 128 disposed through the center of housing 112. Specifically, the central rod 128 is disposed through an aperture defined in the top surface 146 of the housing 112 in a fixed or stationary position. Threaded over the distal end of the central rod 128 is an adjustment unit 132 which comprises a diaphragm 136 and a selector rod 134 which extends in the distal direction from the bottom surface of the diaphragm 136. Inserted through the proximal end of the central rod 128 is a pump handle 130. The pump handle 130 is inserted through the length of the hollow central rod 28 and its distal end is coupled to the adjustment unit 132, specifically to the diaphragm 136. As seen in FIG. 1, the proximal end of the pump handle 130 is substantially shaped to accommodate the user's first and middle fingers as is further detailed below. Disposed around the circumference of the central rod 128 is a spring 138. The proximal end of the spring 138 is coupled near or at the top of the internal volume while the distal end of the spring 38 is coupled to the top surface of the diaphragm 136.

Figure 15A:
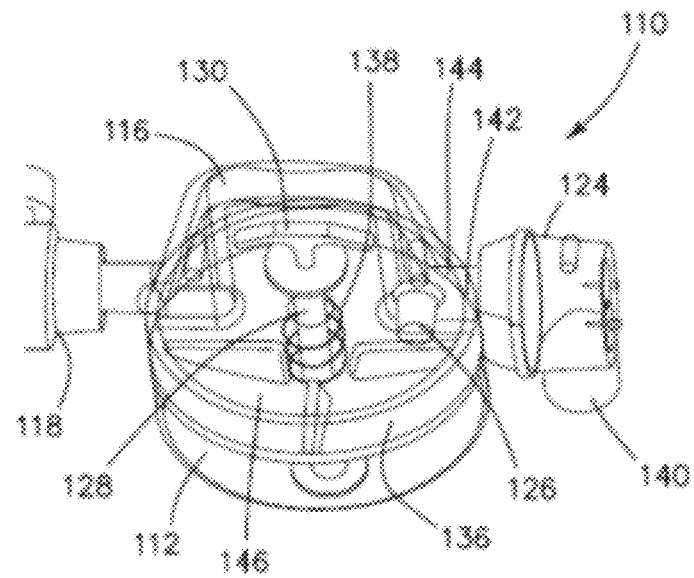
FIG. 15A is a partial cross-sectional perspective view of the alternative embodiment of the resuscitation device seen in FIG. 14 where the oxygen valve is disposed at a vertical orientation.
Figure 15B:
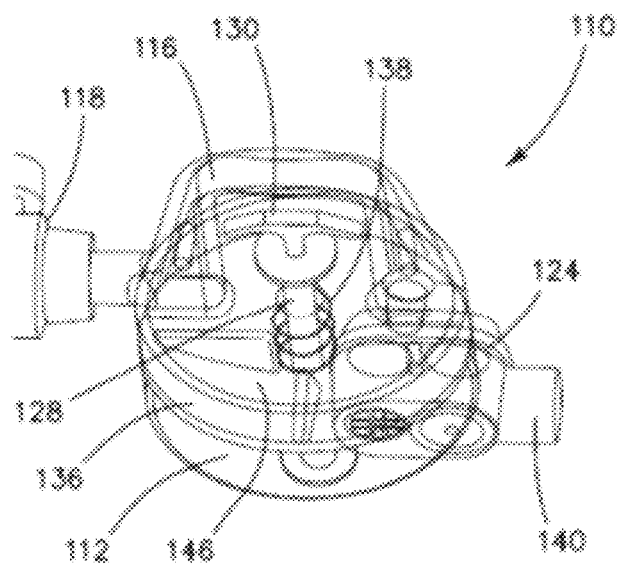
FIG. 15B is a partial cross-sectional perspective view of the alternative embodiment of the resuscitation device seen in FIG. 14 where the oxygen valve is disposed at a horizontal orientation.

Turning to FIGS. 15A and 15B, two different embodiments of the placement of the oxygen valve 124 with respect to the resuscitation device 110 may be seen. In FIG. 15A, the outlet 142 of the oxygen valve 124 inserted into an oxygen aperture 144 defined within a portion of the handle 116. In this embodiment, the oxygen valve 124 is situated or disposed with respect to the housing 112 so that the source inlet 140 is substantially directed in a downward direction relative to the resuscitation device 110. In this configuration, a user is permitted to connect an oxygen source to the source inlet 140 from a location below the device 110. In FIG. 15B, the outlet 142 of the oxygen valve 124 is disposed over the oxygen inlet 126 of the housing 112. In this alternative embodiment, the oxygen valve 124 is situated or disposed with respect to the housing 112 so that the source inlet 140 is substantially perpendicular relative to the longitudinal axis of the oxygen inlet 126. Regardless if the oxygen valve 124 is coupled to the device via the aperture 144 or the oxygen inlet 126, the oxygen valve 124 may be rotated so as to orientate the source inlet 140 to any preferred angle relative the axis of either the aperture 144 or the oxygen inlet 126. By providing a means for a user to selectively couple the oxygen valve 124 to two different positions on the device 110, the user is given increased flexibility for treating the patient by attaching an oxygen source through the source inlet 140 at nearly any angle or orientation, regardless of the surrounding environment or what initial position the user may find the patient in.

Figure 16A:
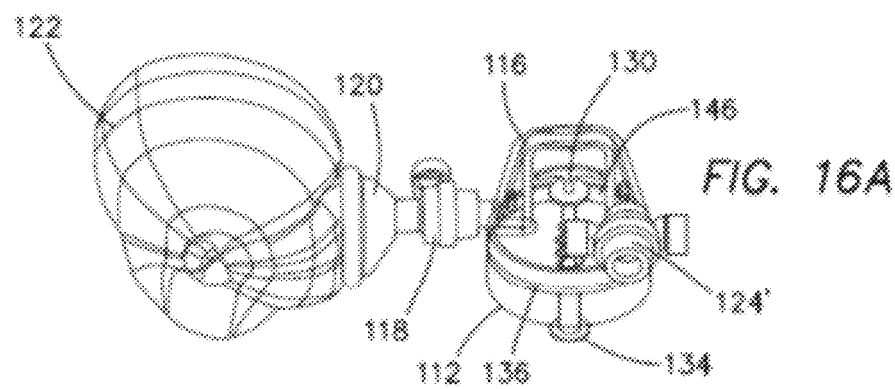
FIG. 16A is a partial cross-sectional perspective view of the alternative embodiment of the resuscitation device seen in FIG. 14 being used on a patient with a first type of oxygen valve.
Figure 16B:
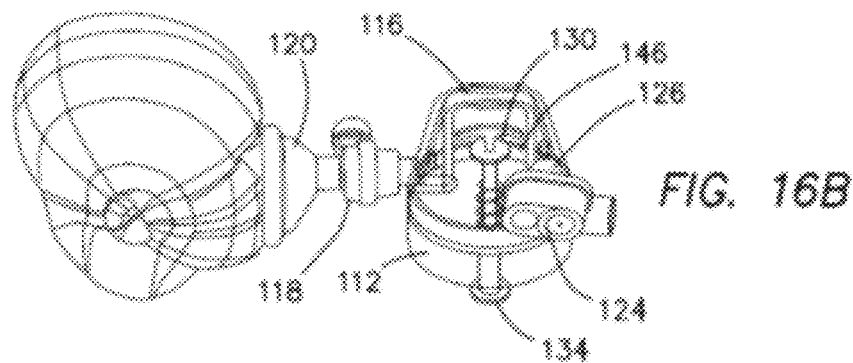
FIG. 16B is a partial cross-sectional perspective view of the alternative embodiment of the resuscitation device seen in FIG. 14 being used on a patient with a second type of oxygen valve.

FIGS. 16A and 16B show two different embodiments of the device 110 in use on a patient 122, namely with an oxygen valve 124 seen in FIG. 16B, or an alternative oxygen valve 124' seen in FIG. 16A. Both configurations of the oxygen valve 124, 124' operate in substantially the same manner with slightly different internal components.

To use the resuscitation device 110, the user approaches the patient 122 and places the face mask 120 of the device 110 over the nose and mouth of the patient 122. The user then connects an oxygen tank or other source to the oxygen valve 124 by connecting a tube or other aperture to the source inlet 140. Alternatively, the user can connect the oxygen source to the oxygen valve 124 before bringing the face mask 120 of the device 110 into contact with the patient 122.

Once the face mask 120 has been properly situated and the oxygen source connected, the user visually inspects the patient and makes an estimation of their total body weight based on their appearance and their apparent height. The user then adjusts the size of the internal volume 114 within the housing 112 by adjusting the vertical position of the diaphragm 136 relative to the top surface 146 of the housing 112. In one embodiment, the diaphragm 136 is held in place within the internal volume 114 by a plurality of contours defined within an internal surface of the internal volume 114, similar to thread of a screw. The user adjusts the relative vertical position of the diaphragm 136 by gripping the selector rod 34 and rotating it in a first direction, thereby moving diaphragm 136 vertically along the internal surface of the internal volume 114. The direction of the diaphragm's 136 movement depends on the orientation of the threads defined within the housing 112. To move the diaphragm 136 in the opposite direction, the user rotates the selector rod 134 in a second direction which is opposite to the first direction. The contours defined within the internal surface of the internal volume 114 are such that the diaphragm 136 is free to traverse vertically up and down through the internal volume 114 when actuated as is discussed in further detail below.

Other embodiments of how the diaphragm 136 may be selectively adjusted within the internal volume 114 includes but is not limited to the central rod 128 and selector rod 134 comprising a hydraulic element disposed between them so as to provide a sufficient stiffness or rigidity such that each time the user moves the selector rod 134 up or down, the diaphragm 136 remains at that position for the duration that the device 110 is being used on the patient 122. For example, to move the diaphragm 136 in the upward direction, the user grips the selector rod 134 and pushes upward, thereby pushing the diaphragm 136 over the central rod 128 which telescopes or is otherwise inserted into the upwardly moving selector rod 134. Once the proper level has been reached, the user releases the selector rod 134 and the hydraulic pressure between the central rod 28 and selector rod 134 maintains the diaphragm 136 in a static position relative the central rod 128 for the duration of use of the resuscitation device 10. To move the diaphragm 136 back in the downward direction, the user pulls the selector rod 134 downward until a new desired position is reached, the hydraulic pressure between the central rod 128 and the selector rod 134 again providing the force necessary to maintain the diaphragm 136 at a fixed position relative to the central rod 128.

Regardless of the means used to adjust the vertical position of the diaphragm 136, once an estimation of the body weight of the patient has been made, the user moves the diaphragm 136 within the housing 112 to create a properly sized internal volume 114 that is specific to the patient being treated. Specifically, a plurality of marked lines or symbols are disposed on the external surface of the housing 112, each of the plurality of marked lines representing a pre-determined or pre-measured volume of air that is contained between the top surface 146 of the housing 112 and the specific point on the housing 112 in which that corresponding marked line is located. Each of the plurality of marked lines is labeled in one embodiment with a weight amount which corresponds to the patient. For example, the first of the plurality of marked lines relative to the top surface 146 of the housing 112 comprises a "45 kg" label, while a second marked line located vertically downward from the first marked line may comprise a "55 kg" label and so on for each of the plurality of marked lines with each subsequent marked line comprising a larger and larger weight label. When the diaphragm 136 is level with any of the marked lines, the volume of air contained within the internal volume 114 created by the diaphragm 136 and the top surface 146 of the housing 112 is ideal for a patient who matches the weight label corresponding to that specific marked line. Specifically, if the diaphragm 136 is disposed at a line marked with a "45 kg" label, the volume of air disposed in the internal volume 114 is about 315 ml, thereby creating an ideal tidal volume for that specific patient at about 6-8 ml per kilogram of body weight. Conversely, if the diaphragm 136 is disposed at a line marked with a "115 kg" label, the volume of air disposed in the internal volume 114 is about 805 ml, thereby providing the larger patient with a larger tidal volume.

It should be noted that the marked lines can be labeled with any relevant or informative alphanumeric phrase, wording, or symbols which conveys a specified volume or tidal volume that will be delivered when the diaphragm 36 is actuated from that specific point. It is therefore expressly understood that that labels can comprise something other than what is explicitly discussed above, namely a weight such as "45 kg", without departing from the original spirit and scope of the invention.

With the diaphragm 136 adjusted to the required level, the user is ready to begin delivering tidal breaths to the patient. The user, with the palm of their hand on the handle 116, then grips the pump handle 130 by preferably hooking their first and middle fingers around the T-shaped proximal end of the pump handle 130. The user then pulls upward on the pump handle 130 by squeezing their fingers and palm together, thereby bringing the pump handle 130 towards the handle 116. Because the distal end of the pump handle 130 is disposed through the central rod 138 and coupled to the diaphragm 136 and selector rod 134, the diaphragm 136 is also pulled upward a corresponding amount. At the same time the diaphragm 36 moves upward through the housing 112, the spring 138 disposed between the diaphragm 136 and the top surface 146 of the housing 112 is compressed. As the diaphragm 136 moves vertically upward through the housing 112, the air within the internal volume 114 is pushed upward through and out of the housing 112 through the patient valve 118 and into the face mask 120. After the user has brought the diaphragm 136 to or near the top surface 146 of the housing 112, the full volume of air within the internal volume 114 has been delivered to the patient and the user then relaxes their grip on the pump handle 130. The compressed spring 138 is then allowed to expand and push the diaphragm 136 back in the distal direction down the vertical height of the housing 112. As the internal volume 114 is increased, a vacuum is created within the housing 112 which draws fresh air or oxygen through the oxygen valve 124, 124'. The diaphragm 36 and selector rod 134 continue to move downward through the housing 112 until reaching its original starting point. At this point, the user has completed one actuation of the resuscitation device 110 and has delivered one tidal breath to the patient.

The user continues to actuate the resuscitation device 110 by repeatedly pulling upward on the pump handle 130 to deliver the air contained within the internal volume 114 and then letting the spring 138 expand and push back the diaphragm 136 to its original position which draws fresh oxygen through the oxygen valve 124 for the next tidal breath. Air delivered to the face mask 120 is inhaled or otherwise enters the patient's oral airway while the patient's exhalation breaths are released into the surrounding environment via the patient valve 118 as is known in the art.

The user continues to operate the resuscitation device 110 for as long as the user deems necessary for the patient's treatment or until additional medical personnel can arrive and further asses the patient. If the user discovers that they have made a mistake in assessing the patient's body weight, the user may immediately stop actuation of the pump handle 130 and change the size of the internal volume 114 to a more appropriate value by adjusting the location of the diaphragm 136 as discussed above. Once properly readjusted, the user may then resume delivering tidal breaths to the patient 122 by actuating the pump handle 130. Once treatment is completed, the user removes the resuscitation device 110 from the patient's vicinity by pulling the face mask 120 away from the nose and mouth of the patient 122.

It can be seen therefore that the resuscitation device 110 allows a user to quickly and efficiently provide a volume of oxygen to a patient in need which is specifically tailored or optimized for that specific patient. In other words, the resuscitation device 110 permits a user to selectively adjust the tidal breaths delivered to patients of any size, thereby preventing over ventilating the patient and causing possible further injury to the patient. Because the internal volume 114 of the resuscitation device 110 can be adjusted, no additional or extraneous resuscitation bags or components are needed for differently sized patients, thereby increasing the ease of use of the device while also saving critical storage space.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A device for selecting a tidal volume to be delivered to a patient comprising:
   a stationary frame;
   a moving frame which at least partially encloses the stationary frame;
   a bellows comprising two opposing ends, a first opposing end coupled to the stationary frame and a second opposing end coupled to the moving frame;
   a slide selector disposed between the moving frame and the stationary frame;
   an oxygen valve coupled to the second opposing end of the bellows; and
   a patient valve coupled to the stationary frame,
   wherein the stationary frame comprises a stop configured to interact with a flat edge disposed on the slide adjuster.

2. The device of claim 1 wherein the slide selector is selectively coupled to a plurality of teeth disposed on the moving frame.

3. The device of claim 1 wherein the moving frame comprises a slit defined in a top surface of the moving frame, and wherein the slide selector comprises a thumb depress and a marker which extend from between the moving frame and the stationary frame through the slit.

4. The device of claim 3 wherein the top surface of the moving frame comprises a measurement table disposed on either lateral side of the slit.

5. The device of claim 1 wherein the moving frame comprises a cavity for accommodating the slide selector and wherein the stationary frame comprises a stop which is configured to interact with a flat edge of the slide selector.

6. The device of claim 1 wherein the slide selector comprises an upper tine and a lower tine, the upper tine and the lower tine being coupled together to form a resilient spring.

7. The device of claim 6 wherein the upper tine of the slide selector comprises a pawl and a thumb depress disposed on a proximal end of the upper tine.

8. The device of claim 1 wherein the bellows is in fluidic communication with a hollow volume defined within the stationary frame and with the oxygen valve coupled to the second opposing end of the bellows.

9. The device of claim 1 wherein the stationary frame comprises a handle and wherein the moving frame comprises a traverse, the traverse comprising a concave interior configured to accommodate a protrusion disposed on the handle.

10. A method for adjusting a tidal volume delivered to a patient by a user with a device, the method comprising:
    estimating a weight of the patient;

actuating a slide selector disposed between a moving frame and a stationary frame of the device;

disposing the moving frame at a first position relative to a stationary frame as dictated by the position of the slide selector;

moving the moving frame in a proximal direction toward the patient to a second position relative to the stationary frame;

delivering a volume of oxygen to the patient from a bellows coupled between the moving frame and the stationary frame;

moving the moving frame in a distal direction away from the patient back to the first position relative to the stationary frame; and refilling the bellows with a new volume of oxygen, wherein actuating the slide selector disposed between the moving frame and the stationary frame of the device comprises pushing or pulling the slide selector within a cavity defined within the moving frame.

11. The method of claim 10 wherein actuating the slide selector disposed between a moving frame and a stationary frame of the device comprises:

pressing downward on a thumb depress disposed on a upper tine of the slide selector to move a pawl disposed on the upper tine off of a plurality of teeth disposed on an interior surface of the moving frame;

moving the slide selector either proximally or distally relative to the moving frame and the stationary frame; and releasing the thumb depress to allow the upper tine to move upward and reinsert the pawl into the plurality of teeth disposed on the interior surface of the moving frame.

12. The method of claim 10 wherein pushing or pulling the slide selector within the cavity defined within the moving frame comprises simultaneously moving a thumb depress and a marker disposed on the slide selector through a slit defined in the moving frame.

13. The method of claim 10 wherein moving the moving frame in a proximal direction toward the patient to a second position relative to the stationary frame comprises compressing the bellows disposed between the moving frame and the stationary frame.

14. The method of claim 10 wherein moving the moving frame in a proximal direction toward the patient relative to the stationary frame comprises disposing a concave interior defined within a traverse within the moving frame over a protrusion disposed on a handle within the stationary frame.

15. The method of claim 10 wherein delivering a volume of oxygen to the patient from a bellows coupled between the moving frame and the stationary frame comprises directing the volume of oxygen from an oxygen valve integrated into the bellows through a hollow volume defined within the stationary frame and into a patient valve coupled to the stationary frame.

16. The method of claim 10 wherein moving the moving frame in the distal direction away from the patient relative to the stationary frame comprises allowing the bellows to expand and push the moving frame distally away from the stationary frame.

17. The method of claim 16 further comprising allowing the bellows to expand until a flat edge of the slide selector makes contact with a stop disposed on the stationary frame.

18. The method of claim 10 further comprising coupling a resuscitation bag and an oxygen tube to an oxygen valve integrated into a distal end of the bellows.

* * * * *